(12) United States Patent
Agrez

(10) Patent No.: US 9,765,113 B2
(45) Date of Patent: Sep. 19, 2017

(54) METHODS AND AGENTS FOR THE TREATMENT OF CANCER

(71) Applicant: INTERK PEPTIDE THERAPEUTICS LIMITED, Newcastle (AU)

(72) Inventor: Michael V. Agrez, Katoomba (AU)

(73) Assignee: INTERK PEPTIDE THERAPEUTICS LIMITED, Newcastle (AU)

( * ) Notice: Subject to any disclaimer, the term of this patent is extended or adjusted under 35 U.S.C. 154(b) by 0 days.

(21) Appl. No.: 14/569,321

(22) Filed: Dec. 12, 2014

(65) Prior Publication Data

US 2015/0284428 A1    Oct. 8, 2015

Related U.S. Application Data

(62) Division of application No. 10/575,736, filed as application No. PCT/AU2004/001416 on Oct. 15, 2004, now abandoned.

(30) Foreign Application Priority Data

Oct. 17, 2003  (AU) .............................. 2003905726

(51) Int. Cl.
C07K 7/06      (2006.01)
C07K 14/705    (2006.01)
A61K 38/00     (2006.01)

(52) U.S. Cl.
CPC .......... *C07K 7/06* (2013.01); *C07K 14/70546* (2013.01); *A61K 38/00* (2013.01)

(58) Field of Classification Search
None
See application file for complete search history.

(56) References Cited

U.S. PATENT DOCUMENTS

| | | |
|---|---|---|
| 5,593,884 A | 1/1997 | Karin et al. |
| 5,807,746 A | 9/1998 | Lin et al. |
| 5,877,282 A | 3/1999 | Nadler et al. |
| 5,962,643 A | 10/1999 | Sheppard et al. |
| 6,007,991 A | 12/1999 | Sivaraman et al. |
| 6,043,339 A | 3/2000 | Lin et al. |
| 6,248,558 B1 | 6/2001 | Lin et al. |
| 6,312,956 B1 | 11/2001 | Lane |
| 6,339,148 B1 | 1/2002 | Sheppard et al. |
| 6,432,680 B1 | 8/2002 | Lin et al. |
| 6,495,518 B1 | 12/2002 | Hawiger et al. |
| 6,576,432 B1 | 6/2003 | Sheppard et al. |
| 6,596,277 B1 | 7/2003 | Sheppard et al. |
| 6,639,056 B2 | 10/2003 | Sheppard et al. |
| 6,699,703 B1 | 3/2004 | Doucette-Stamm |
| 6,780,843 B2 | 8/2004 | Lin et al. |
| 6,787,322 B2 | 9/2004 | Sheppard et al. |
| 6,800,744 B1 | 10/2004 | Doucette-Stamm |
| 2004/0147435 A1 | 7/2004 | Hawiger et al. |

FOREIGN PATENT DOCUMENTS

| | | |
|---|---|---|
| WO | WO 91/19008 | 12/1991 |
| WO | WO 92/12236 | 7/1992 |
| WO | WO 95/34295 | 12/1995 |
| WO | WO 98/16241 | 4/1998 |
| WO | WO 99/09214 | 2/1999 |
| WO | WO 99/49879 | 10/1999 |
| WO | WO 00/59549 | 10/2000 |
| WO | WO 01/00677 | 1/2001 |
| WO | WO 01/37821 | 5/2001 |
| WO | WO 02/051993 | 7/2002 |

OTHER PUBLICATIONS

Jones (Pharmacogenomics Journal, 1:126-134, 2001).*
Tosatto et al (Current Pharmaceutical Design, 12:2067-2086, 2006).*
GB Search Report.
Agrez, M., et al., "The $\alpha_v\beta_6$ integrin promotes proliferation of colon carcinoma cells through a unique region of the $\beta_6$ cytoplasmic domain". J. Cell. Biol. 127, No. 2, pp. 547-556 (1994).
Agrez, M.V., "Cell adhesion molecules and colon cancer", A.N.Z.J. Surgery 66, 789-796 (1996).
Agrez, et al., "The $\alpha v\beta 6$ integrin induces gelatinase B secretion in colon cancer cells", Int. J. Cancer 81 (1), 90-7 (1999).
Agrez, M.V. et al., "Colorectal cancer and the integrin family of cell adhesion receptors: current status and future directions", European Journal of Cancer 30A, 2166-2170 (1994).
Agrez, M.V. et al., "Multiplicity of fibronectin-binding a v integrin receptors in colorectal cancer", Br. J. Cancer 73, 887-892 (1996).
Ahmed, N. et al., "Direct integrin $\alpha_v\beta_6$—ERK binding: implications for tumour growth". Oncogene 21, 1370-1380 (2002).
Bookstein, R. et al, "p53 gene therapy in vivo for hepatocellular and liver metastatic colorectal cancer", Seminars Oncol. 23, 66-77 (1996).
Boudreau, N.J and Jones, P.L., "Extracellular matrix and integrin signalling: the shape of things to come". Brochem, J. 339, 481-488 (1999).
Boulton, T.G., et al., "ERKs: a family of protein-serine/threonine kinases that are activated and tyrosine phosphorylated in response to insulin and NGF", Cell 65, 663-675 (1991).
Boulton, T.G., et al., "Mitogen-activated protein kinase 1," (EC 2.7.1) (1991) (Swiss Prot Acc No. P27703).
Bruess, J.M., et al., "The integrin a 6 β 1, is necessary for the matrix-dependent activation of FAK and MAP Kinase and the migration of human hepatocarcinoma cells," Hepatology, Jul 34(1), 42-9 (2001).

(Continued)

*Primary Examiner* — Brad Duffy

(74) *Attorney, Agent, or Firm* — Bryan D. Zerhusen; Locke Lord LLP

(57) ABSTRACT

There are disclosed methods for prophylaxis or treatment of cancer in a mammal. The methods comprise administering an effective amount of an agent to the mammal, which binds to a MAP kinase or an integrin such that binding of the MAP kinase to the integrin is inhibited.

8 Claims, 20 Drawing Sheets

(56) References Cited

OTHER PUBLICATIONS

Carlone, V. et al., The Integrin, $\alpha_6\beta_1$, is necessary for the matrix-dependent activation of FAK and MAP kinase and the migration of human hepatocarcinoma cells. Hepatology. vol. 34, No. 1, 42-49 (2001).
Chen et al,. "Distinct structural requirements for interaction of the integrins a5β1, avβ5, and avβ6 with central cell binding domain in fibronectin," Cell Adhesion and Communication, vol. 4, No. 4-5, pp. 237-250 (1996).
Cone et al., "Effects of β subunit cytoplasmic domain deletions on the recruitment of the integrin avβ6 to focal contact", Cell Adhesion and Communication, vol. 2, pp. 101-113 (1994).
Coppolino et al., "Bi-directional signal transduction by integrin receptors," The International Journal of Biochemistry & Cell Biology, vol. 32, pp. 171-188 (2000).
Coppolino, M. et al., "Inducible interaction of integrin alpha 2 beta 1 with calreticulin. Dependence of the activation state of the integrin", J. Biol. Chem. 270, 23132-23138 (1995).
Dedhar, S. and Hannigan, G.E., "Integrin cytoplasmic interactions and bidirectional transmembrane signalling". Curr. Op. Cell Biol. vol. 8, No. 5, 657-669 (1996).
Dixit et al., "Identification of a sequence within the integrin β6 subunit cytoplasmic domain that is required to support the specific effect of avβ6 on proliferation in three-dimensional culture", J Biol. Chem., vol. 271, No. 42, pp. 25976-25980 (1996).
Eliceiri, B.P., et al., "The role of av integrins during angiogenesis: insights into potential mechanisms of action and clinical development," J Clin Invest (1999), 103(9), 1227-30.
Eliceiri, B.P., et al., "Integrin avβ3 requirement for sustained mitogen activated protein kinase activity during angiogenesis," J Cell Biol (1998), 140(5): 1255-63.
Erker, J.C. et al., Database GenBank 'Online', "Polyprotein GB virus c/Hepatitis C virus", Database Accession No. AAC55951 (Nov. 13, 1996) (Abstract).
Fodstad, O. et al., Database Geneseq 'Online', "CAPL gene 5' splice site antisense oligonucleotide", Database Accession No. AAT33333 (Nov. 12, 1996).
Friedlander, M., et al., "Definition of two angiogenic pathways by distinct a v integrins," Science (995), 270(5241): 1500-2.
Gamble, J. R. et al., "Regulation of in vitro capillary tube formation by anti-integrin antibodies", J. Cell Biol. 121, 931-943 (1993).
Garrington, T.P. et al., "Organization and regulation of mitogen-activated protein kinase signaling pathways", Curl. Opin. Biol. 11, 211-218 (1999).
Giancotti, F.G. et al., "Integrin signaling", Science 285, 1028-1032 (1999). Gorgziglia and Kapikian, J., Virol. 66, 4407-4412 (1992).
Gonzalez, F.A., "*H sapiens* 40kDa protein kinase related to rat ERK2," (1992) (GenPept Acc No. CAA77753).
Gorziglia, M. And Kapikian, A.Z., "Expression of the OSU rotaravirus outer capsid protein VP4 by an adenovirus recombinant". J. Virol., pp. 4407-4412, Jul. 1992.
Gotoh et al., "Cross-Linking of Integrins Induces Tyrosine Phosphorylation of the Proto-Oncogene Product Vav and the Protein Tyrosine Kinase Syk in Human Factor-dependent Myeloid Cells", Cell Growth and Differentiation, vol. 8, pp. 721-729 (1997).
Grammer, T.C. et al., "Evidence for MEK-independent pathways regulating the prolonged activation of the ERK-MAP kinases", Oncogene 14, 1635-1642 (1997).
Gu, J. et al., "Tumor suppressor PTEN inhibits integrin—and growth factor—mediated nitrogen activated protein (MAP) kinase signalling pathways". J. Cell Biol. vol. 143, No. 5, 1375-1383 (1998).
Guan, J.L. et al., "Regulation of focal adhesions-associated protein tyrosine kinase by both cellular adhesion and oncogenic transformation", Nature 358, 690-692 (1992).
Gupta, K., et al., "VEGF prevents apoptosis of human microvascular endothelial cells via opposing effects on MAPK/ERK and SAPK/JNK signaling," Exp Cell Res (1999), 247(2): 495-504.
Hannigan, G.E. et al., "Regulation of cell adhesion and anchorage-dependent growth by a new beta 1-integrin-linked protein kinase", Nature 379, 91-96 (1996).
von Heijne, G., "The Signal Peptide". Topical Review. J. Membrane Biol. 115, 195-201 (1990).
Hemler, M.E., "Integrin associated proteins", Curr. Opin. Biol. 10, 578-585 (1998).
Hergott, G.J. et al., "Inhibition of retinal pigment epithelial cell migration and proliferation with monoclonal antibodies against the beta 1 integin subunit during wound healing in organ culture", Invest. Opthalmol. Vis. Sci. 34, 2761-2768 (1993).
Horwitz, A. et al., "Interaction of plasma membrane fibronectin receptor with a talin-a transmembrane linkage", Nature 320, 531-533 (1986).
Howe, A. et al., "Integrin signaling and cell growth control", Curr. Opin. Biol. 10, 220-231 (1998).
Hughes, P.E. and Pfaff, M., "Integrin affinity modulation". Trends. Cell Biol. vol. 8, No. 9, 359-364 (1998).
Ishii, T., et al., "Integrin-linked kinase controls neurite outgrowth in N1E-115 neuroblastoma cells," J. Biol. Chem. 276(46): 42994-43003 (2001).
Johnson O.L. and Tracey, M.A., Encyclopaedia of Controlled Drug Delivery. vol. 2, pp. 816-833. Edith Mathiowitz, John Wiley & Sons, Inc. New York (1999).
Kerr, et al., "Novel small a v integrin antagonists: Comparative anti-cancer efficacy with known angiogenesis inhibitors", Anticancer Res 19 (2A), 959-68, (1999).
Knezevic, I. et al., "Direct binding of the platelet integrin alpha lib beta 3 (Pella) to talin. Evidence that interaction is mediated through the cytoplasmic domains of both alpha IIb and beta 3", J. Biol. Chem. 271, 16416-16421 (1996).
Kornberg, L. et al., "Cell adhesion or integrin clustering increases phophorylation of a focal adhesion-associated tyrosine kinase", J. Biol. Chem. 267, 23439-23442 (1992).
Lin et al., "Integrin-mediated Activation of MAP Kinase Is Independent of FAK: Evidence for Dual Integrin Signaling Pathways in Fibroblasts", J. Cell. Biol., vol. 136, No. 6, (1997).
Lin, Y-Z et al., "Inhibition of nuclear translocation of transcription factors NF—κB by a synthetic peptide containing a cell membrane-permeable motif and nuclear localization sequence". J. Biol. Chem. vol. 230, No. 24, 14255-14258 (1995).
Liu, S., et al., "Binding of paxillin to $\alpha_4$ integrins modifies integrin-dependent biological responses". Nature. vol. 402, 666-681 (1999).
Liu, X-Y, et al., "Identification of a functionally important sequence in the cytoplasmic tail of integrin $\beta_3$ by using cell-permeable peptide analogs". Proc. Natl. Acad. Sci. USA. vol. 93, 11819-11824 (1996).
Loftus, J.C et al., "Integrin-mediated cell adhesion: the extracellular face", J. Biol. Chem. 269, 25235-25238 (1994).
Lub, M., et al; "Cytoplasmic tails of $\beta_1$, $\beta_2$, and $\beta_7$ integrins differentially regulate LFA-1 function in K562 cells". Mol. Biol. Cell, vol. 8, 719-728 (1997).
Maniero, F., et al., "The coupling of $\alpha_6\beta_4$ integrin to Ras-MAP kinase pathways mediated by Shc controls keratinocyte proliferation". EMBO J. vol. 16, No. 9, 2365-2375 (1997).
Marcantonio, E.E., et al., "Mapping of the functional determinants of the integrin $\beta_1$ cytoplasmic domain by site-directed mutagenesis". Cell Reg. vol. 1, 591-604 (1990).
Mastrengelo, A.M., et al., "Amino acid motifs required for isolated β cytoplasmic domains to regulate 'in trans' $\beta_1$ integrin conformation and function in cell attachment". J. Cell. Science, 112, 217-229 (1999).
Meurers, B.H. et al., Database GenBank 'Online'. "Myosin heavy chain 12 '*Homo sapiens*'", Database Accession No. CAA69036 (Jan. 8, 1997) (Abstract).
Miranti, C.K. et al., "Protein Kinase C regulates integrin-induced activation of the extracellular regulated kinase pathway upstream of Shc", J. Biol. Chem. 274, 10571-10581 (1999).
Niu, J., et al., "Integrin expression in colon cancer cells is regulated by the cytoplasmic domain of the $\beta_6$ integrin submit". Int. J. Cancer. 99, 529-537 (2002).
Oda, K. et al., Database GenBank 'Online', "Coxll intron2 ORF Marchantia polymorpha!", Database Accession No. AAC09431 (Apr. 2, 1998) (Abstract).

(56) References Cited

OTHER PUBLICATIONS

Otey, C.A. et al., "An interaction between alpha-actinin and beta 1 integrin subunit in vitro", J. Cell Biol. 111, 721-729 (1990).
O'Toole, T.E., et al., "Regulation of integrin affinity states through an NPXY motif in the β subunit cytoplasmic domain". J. Biol. Chem. vol. 270, No. 15, 8553-8558 (1995).
Pagès, G., et al., "Signaling angiogenesis via p42/p44 MAP kinase cascade," Ann NY Acad Sci, 902: 187-200, (2000).
Pardi, R., et al., "Conserved regions in the cytoplasmic domains of the leukocyte integrin $\alpha_L\beta_2$ are involved in endoplasmic reticulum retention, dimerization, and cytoskeletal association". J. Immunol. vol. 155, No. 3, 1252-1263 (1995).
Patil, S., et al., "A double mutation of the NPLY motif in the integrin β3 cytoplasmic tail abolishes post-ligand binding events of $\beta_3$ integrins". vol. 7, No. Suppl. p. 248A (1996) (Abstract).
Payne, D.M. et al., "Identification of the regulatory phosphorylation sites in pp42/mitogen-activated protein kinase (MAP kinase)", EMBOJ 10, 885-892 (1991).
Pfaff, M. et al., "Integrin beta cytoplasmic domains differentially bind to cytoskeletal proteins", J. Biol. Chem. 273, 6104-6109 (1998).
Pillinger, M., et al., "Modes of action of aspirin-like drugs: Salicylates inhibit Erk activation and integrin-dependent neutrophil adhesion". Proc. Natl. Acad. Sci. USA. vol. 95, 14540-14545 (1998).
Redlitz, A., et al., "Angiostatin diminishes activation of the mitogen-activated protein kinases ERK-1 and ERK-2 in human dermal microvascular endothelial cells." J Vasc Res, 36(1): 28-34, (1999).
Reszka, A.A. et al., "Identification of amino acid dequences in the integrin beta 1 cytoplasmic domain implicated in cytoskeletal association", J. Cell Biol. 117, 1321-1330 (1992).
Roberts, M.S., et al., "ERK1 associates with $\alpha_v\beta_3$ integrin and regulates cell spreading on vitronection". J. Biol. Chem. vol. 278, No. 3, 1975-1985 (2003).
Rojiani, M.V. et al., "In vitro interaction of a polypeptide homologous to human Ro/SS-A antigen (calreticulin) with a highly conserved amino acid sequence in the cytoplasmic domain of integrin alpha subunits", Biochemistry 30, 9859-9866 (1991).
Schaller, M.D. et al., "Focal adhesion kinase and paxillin bind to peptides mimicking beta integrin cytoplasmic domains", J. Cell Biol. 130, 1181-1187 (1995).
Sebolt-Leopold, J.S., et al., "Blockade of the MAP kinase pathway suppresses growth of colon tumors in vivo". Nature Medicine. vol. 5, No. 7, 810-816 (1999).
Sheppard, D. et al., "Complete amino acid sequence of a novel integrin β subunit (β6) identified in epithelial cells using the polymerase chain reaction", J. Biol. Chem. 265, 11502-11507 (1990).
Sugiura, N., et al., "*Mus muculus* DNA for ERK2," exon 7. (GenPept Acc No. BAA22620) (1997) (Abstract).
Swanson, R. et al., Database GenBank 'Online', "UL97 homolog Rhesus cytomegalovirus!", Database Accession No. AAC05259 (Mar. 7, 1998) (Abstract).
Tada, M. et al., Database GenBank 'Online', "Homeobox protein B1X3 'Xenopus laevis'", Database Accession No. AAC61703 (Sep. 29, 1998) (Abstract).
Tahiliani, P.D., et al., "The role of conserved amino acid motifs within the integrin $\beta_3$ cytoplasmic domain in triggering focal adhesion kinase phosphasylation". J. Biol. Chem. vol. 272, No. 12, 7892-7898 (1997).
Tanaka, K., et al., "Roles of extracellular signal-regulated kinase 1/2 and p38 nitrogen-activated protein kinase in the signal transduction of basic fibroblast growth factor in endothelial cells during angiogenesis". Jpn. J. Cancer Res. 90, 647-654 (1999).
Trikha, et al., "Role of aIIβ3 integrin in prostate cancer metastasis", Prostate 35 (3), 185-92, (1998).
Townsend, P.A., et al; "β1 integrin antisense oligodeoxynucleotides: utility in controlling osteoclast function". Eur. J. Cell. Biol. vol. 78, 485-496 (1999).
Varner, J.A. et al., "Integrin alpha 5 beta 3 expression negatively regulates cell growth: reversal by attachment to fibronectin", Mol. Biol. Cell 6, 725-740 (1995).
Vignoud, L., et al., "NPXY motifs control the recruitment of the $\alpha_5\beta_1$ integrin in focal adhesions independently of the association of talin with the $\beta_1$ chain". J. Cell. Sci. 110, 1421-1430 (1997).
Wang, A. et al., "Differential regulation of airway epithelial integrins by growth factors", Am. J. Respira. Cell & Mol. Biol. 15, 664-672 (1996).
Wary, K.K. et al., "The adaptor protein Shc couples a class of integrins to the control of cell cycle progression", Cell 87, 733-743 (1996).
Weinacker et al. Role of the integrin alpha v beta 6 in cell attachment to fibronectin. J. Biol. Chem. 269:6940-6948, (1994).
Yokosaki et al., "Differential Effects of the Integrins aIβ, avβ, avβ6 on Cell Proliferative Responses to Tenascin: Roles of the β Subunit Extracellular and Cytoplasmic Domains," J. Biol. Chem., vol. 271, No. 39, pp. 24144-24150, (1996).
Yu, Y., et al., "Map Kinases, phosphatidylinositol 3-kinase, and p70 S6 kinase mediate the mitogenic response of human endothelial cells to vascular endothelial growth factor," J Cell Physiol, 178(2): 235-46, (1999).
Zage, P.E. and Marcantonio, E. E., "The membrane proximal region of the integrin β cytoplasmic domain can mediate oligomerization". Cell. Adh. and Comm. vol. 5, 335-347 (1998).
Zhang, et al., "Retroviral transfer of antisense integrin α6 or α8 sequences results in laminar redistribution or clonal cell death in developing brain", J. Neurosci. 18(17), 6928-38, (1998).
Tame (J. Comput. Aided Mol. Des. Mar. 1999; 13(2): 99-108).
Dixon (Proteins. 1997; Suppl 1: 198-204).
Lensink et al. (Proteins. 2007; 69: 704-718).
Skolnick et al. (Trends in Biotechnology 2000; 18: 34-39).

* cited by examiner

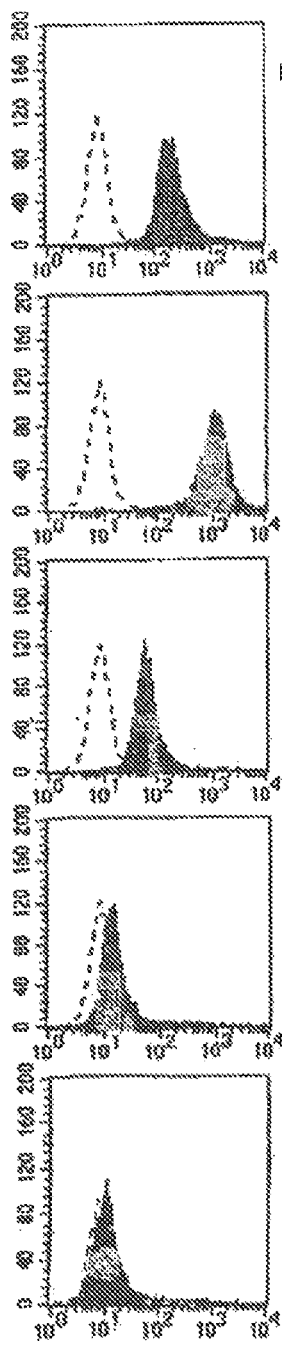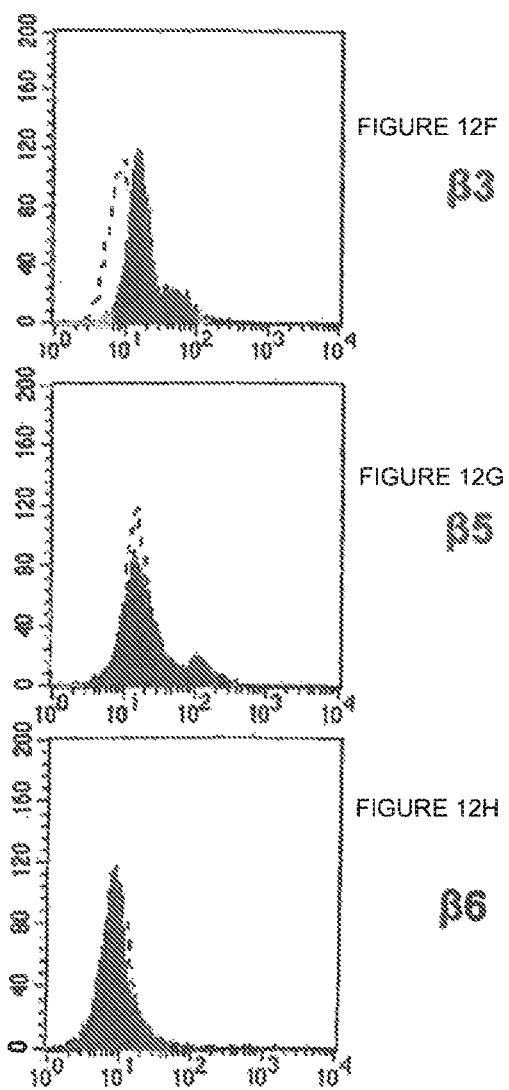

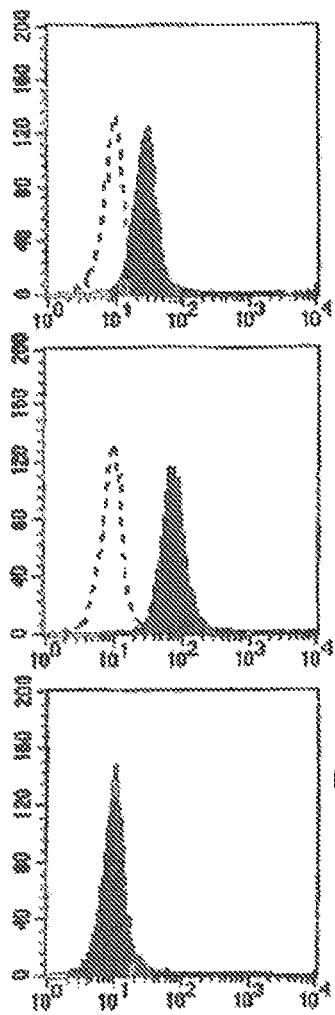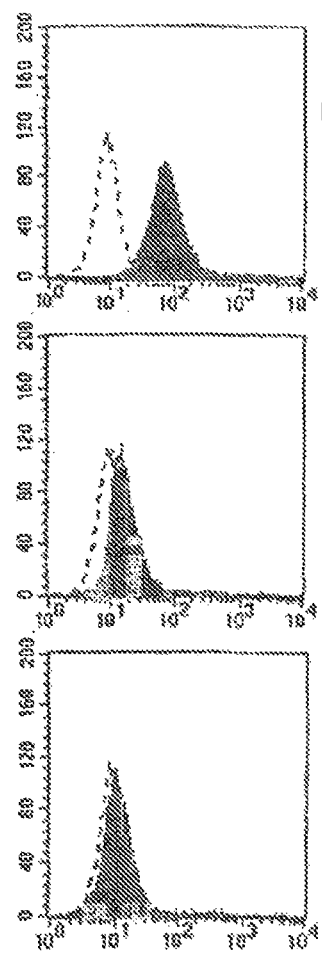
FIGURE 12I
FIGURE 12J
FIGURE 12K
FIGURE 12L
FIGURE 12M
FIGURE 12N

HT29 Cell Line

H460 Cell Line

β5

β6

WM 115 Cell Line

β3

β5

β6

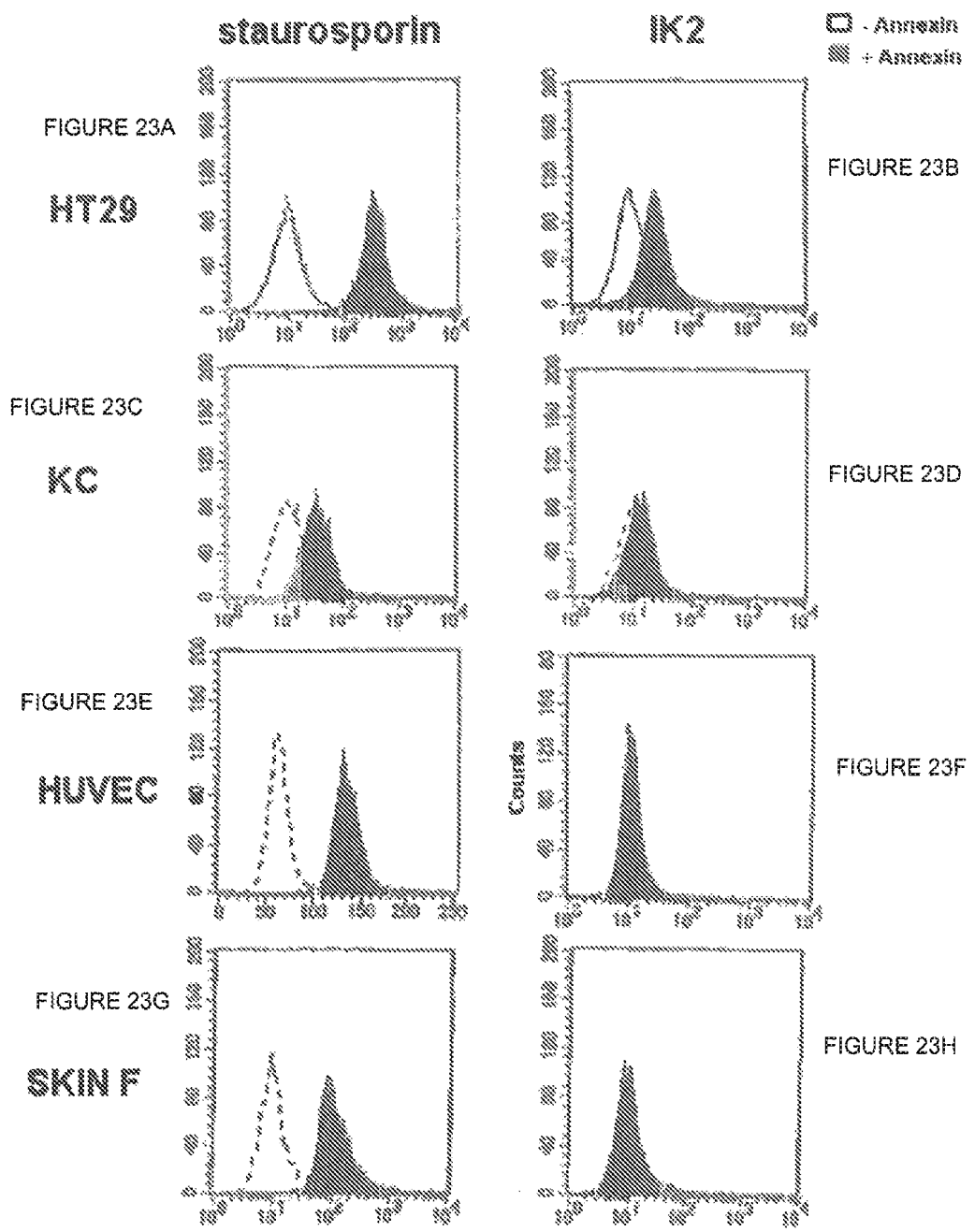

```
SEQUENCE LISTING

<160> NUMBER OF SEQ ID NOS: 33

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ala Val Ala Leu Leu Pro Ala Val Leu Leu Ala Leu Leu Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 2

Val Thr Val Leu Ala Leu Gly Ala Leu Ala Gly Val Gly Val Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ala Val Ala Leu Leu Pro Ala Val Leu Leu Ala Leu Leu Ala Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Lys Ala Lys Trp Gln Thr Gly Thr Asn Pro Leu Tyr Arg
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Arg Ala Lys Trp Asp Thr Ala Asn Asn Pro Leu Tyr Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Arg Ala Arg Tyr Glu Met Ala Ser Asn Pro Leu Tyr Arg
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Lys Ala Lys Asn Pro Leu Tyr Arg
1               5                   10

<210> SEQ ID NO 8
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Arg Ala Lys Asn Pro Leu Tyr Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Arg Ala Arg Asn Pro Leu Tyr Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Glu Lys Leu Lys Asn Pro Leu Phe Lys
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Glu Lys Leu Lys Ser Gln Trp Asn Asn Asp Asn Pro Leu Phe Lys
1               5                   10                  15

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Arg Asp Leu Lys Pro Ser Asn Leu Leu Leu Asn Thr Thr Cys Asp
1               5                   10                  15

Leu Lys Ile Cys Asp Phe Gly Leu Ala Arg
            20                  25

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Pro Ser Asn Leu Leu Asn Thr Thr Cys Asp Leu Lys Ile Cys
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Arg Lys Lys Arg Arg Gln Arg Arg Pro Pro Gln Gly
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gln Ile Lys Ile Trp Phe Gln Asn Arg Arg Met Lys Trp Lys Lys
1               5                   10                  15

Gly

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Ala Val Ala Leu Leu Pro Ala Val Leu Leu Ala Leu Leu Ala Arg
1               5                   10                  15

Ser Lys Ala Lys Asn Pro Leu Tyr Arg
            20                  25

<210> SEQ ID NO 17
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Val Ala Leu Leu Pro Ala Val Leu Leu Ala Leu Leu Ala Arg
1               5                   10                  15

Ser Arg Ala Arg Asn Pro Leu Tyr Arg
            20                  25

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Ala Ala Val Ala Leu Leu Pro Ala Val Leu Leu Ala Leu Leu Ala Pro
1               5                   10                  15

Arg Ser Lys Ala Lys Asn Pro Leu Tyr Arg
            20                  25
```

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Ala Ala Val Ala Leu Leu Pro Ala Val Leu Leu Ala Leu Leu Ala Arg
1               5                   10                  15

Ser Lys Ala Lys Trp Gln Thr Gly Thr Asn Pro Leu Tyr Arg
            20                  25                  30
```

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Trp Gln Thr Gly Thr
1               5
```

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Tyr Glu Met Ala Ser
1               5
```

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Tyr Glu Met Ala Ser
1               5
```

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid

```
<400> SEQUENCE: 23

Asp Leu Xaa Xaa Leu
1               5

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Thr Asp Leu Asp Ser Leu Arg Thr Tyr Thr Leu
1               5                   10

<210> SEQ ID NO 25
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

His Arg Asp Leu Lys Pro Ser Asn Leu Leu Leu Asn Thr Thr Cys Asp
1               5                   10                  15

Leu Lys Ile Cys Asp Phe Gly Leu Ala Arg
            20                  25

<210> SEQ ID NO 26
<211> LENGTH: 52
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Asp Arg Lys Glu Val Ala Lys Phe Glu Ala Glu Arg Ser Lys Ala
1               5                   10                  15

Lys Trp Gln Thr Gly Thr Asn Pro Leu Tyr Arg Gly Ser Thr Ser Thr
            20                  25                  30

Phe Lys Asn Val Thr Tyr Lys His Arg Glu Lys Gln Lys Val Asp Leu
        35                  40                  45

Ser Thr Asp Cys
    50

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gln Trp Asn Asn Asp
1               5

<210> SEQ ID NO 28
<211> LENGTH: 26
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 28

His Arg Asp Leu Lys Pro Ser Asn Leu Leu Asn Thr Thr Cys Asp
1               5                   10                  15

Leu Lys Ile Cys Asp Phe Gly Leu Ala Arg
            20                  25

<210> SEQ ID NO 29
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

His Arg Asp Leu Lys Pro Ser Asn Leu Ala Val Asn Glu Asp Cys Glu
1               5                   10                  15

Leu Lys Ile Leu Asp Phe Gly Leu Ala Arg
            20                  25

<210> SEQ ID NO 30
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Arg Asp Leu Lys Pro Ser Asn Ile Val Val Lys Ser Asp Cys Thr
1               5                   10                  15

Leu Lys Ile Leu Asp Phe Gly Leu Ala Arg
            20                  25

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Thr Val Leu Ala Leu Gly Ala Leu Ala Gly Val Gly Val Gly Arg
1               5                   10                  15

Ser Lys Ala Lys Trp Gln Thr Gly Thr Asn Pro Leu Tyr Arg
            20                  25                  30

<210> SEQ ID NO 32
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Gln Ile Lys Ile Trp Phe Gln Asn Arg Arg Met Lys Trp Lys Lys
1               5                   10                  15

Arg Ser Lys Ala Lys Asn Pro Leu Tyr Arg
            20                  25
```

```
<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Arg Lys Lys Arg Arg Gln Arg Arg Arg Pro Gln Cys Gly
1               5                   10
```

METHODS AND AGENTS FOR THE TREATMENT OF CANCER

CROSS-REFERENCE TO RELATED APPLICATIONS

This application is a divisional of U.S. application Ser. No. 10/575,739, filed Apr. 13, 2006, which is the U.S. national phase application, pursuant to 35 U.S.C. §371, of PCT international application Ser. No. PCT/AU2004/001416 filed Oct. 15, 2004, designating the United States and published in English on Apr. 28, 2005 as publication WO 2005/037308 A1, which claims priority to Australian application Ser. No. 2003905726, filed Oct. 17, 2003. The entire contents of the aforementioned patent applications are incorporated herein by this reference.

FIELD OF THE INVENTION

The present invention relates to methods for modulating cell activity mediated by mitogen activated protein kinases (MAP's) and more particularly, inhibition of the growth and/or the proliferation of cancer cells. There are also provided agents for use in the methods of the invention.

BACKGROUND OF THE INVENTION

The spread of cancer cells involves tumour cell migration through the extracellular matrix scaffold, invasion of basement membranes, arrest of circulating tumour cells, and tumour cell extravasation and proliferation at metastatic sites. Detachment of cells from the primary tumour mass and modification of the peri-cellular environment aid penetration of tumour cells into blood and lymphatic vessels. It is the invasive and metastatic potential of tumour cells that ultimately dictates the fate of most patients suffering from malignant diseases. Hence, tumourigenesis can be viewed as a tissue remodelling process that reflects the ability of cancer cells to proliferate and digest surrounding matrix barriers. These events are thought to be regulated, at least in part, by cell adhesion molecules and matrix-degrading enzymes.

Cell adhesion receptors on the surface of cancer cells are involved in complex cell signalling which may regulate cell proliferation, migration, invasion and metastasis and several families of adhesion molecules that contribute to these events have now been identified including integrins, cadherins, the immunoglobulin superfamily, hyaluronate receptors, and mucins. In general, these cell surface molecules mediate both cell-cell and cell-matrix binding, the latter involving attachment of tumour cells to extracellular scaffolding molecules such as collagen, fibronectin and laminin.

Of all the families of cell adhesion molecules, the best-characterised is the family known as integrins. Integrins are involved in several fundamental processes including leucocyte recruitment, immune activation, thrombosis, wound healing, embryogenesis, virus internalisation and tumourigenesis. Integrins are transmembrane glycoproteins consisting of an alpha ($\alpha$) and beta ($\beta$) chain in close association that provide a structural and functional bridge between extracellular matrix molecules and cytoskeletal components with the cell. The integrin family comprises 17 different $\alpha$ and 8 $\beta$ subunits, and the $\alpha\beta$ combinations are subsumed under 3 subfamilies.

Excluding the leucocyte integrin subfamily that is designated by the $\beta2$ nomenclature, the remaining integrins are arranged into two major subgroups, designated $\beta1$ and $\alpha v$ based on sharing common chains.

In the $\beta1$ subfamily, the $\beta1$ chain combines with any one of nine $\alpha$ chain members ($\alpha$1-9), and the $\alpha$ chain which associates with $\beta1$ determines the matrix-binding specificity of that receptor. For example, $\alpha2\beta1$ binds collagen and laminin, $\alpha3\beta1$ binds collagen, laminin and fibronectin, and $\alpha5\beta1$ binds fibronectin. In the $\alpha v$ subfamily of receptors, the abundant and promiscuous $\alpha v$ chain combines with any one of five $\beta$ chains, and a distinguishing feature of $\alpha v$ integrins is that they all recognise and bind with high affinity to arginine-glycine-aspartate (RGD) sequences present in the matrix molecules to which they adhere.

The current picture of integrins is that the N-terminal domains of $\alpha$ and $\beta$ subunits combine to form a ligand-binding head. This head, containing the cation binding domains, is connected by two stalks representing both subunits, to the membrane-spanning segments and thus to the two cytoplasmic domains. The $\beta$ subunits all show considerable similarity at the amino acid level. All have a molecular mass between 90 and 110 kDa, with the exception of $\beta4$ which is larger at 210 kDa. Similarly, they all contain 56 conserved cysteine residues, except for $\beta4$ which has 48. These cysteines are arranged in four repeating patterns which are thought to be linked internally by disulphide bonds. The $\alpha$-subunits have a molecular mass ranging from 150-200 kDa. They exhibit a lower degree of similarity than the $\beta$ chains, although all contain seven repeating amino acid sequences interspaced with non-repeating domains.

The $\beta$ subunit cytoplasmic domain is required for linking integrins to the cytoskeleton. In many cases, this linkage is reflected in localisation to focal contacts, which is believed to lead to the assembly of signalling complexes that include $\alpha$-actinin, talin, and focal adhesion kinase (FAK). At least three different regions that are required for focal contact localisation of $\beta1$ integrins have been delineated (Reszka et al, 1992). These regions contain conserved sequences that are also found in the cytoplasmic domains of the $\beta2$, $\beta3$, $\beta5$, $\beta6$ and $\beta7$ integrin subunits. The functional differences between these cytoplasmic domains with regard to their signalling capacity have not yet been established.

The integrin $\beta6$ subunit was first identified in cultured epithelial cells as part of the $\alpha v\beta6$ heterodimer, and the $\alpha v\beta6$ complex was shown to bind fibronectin in an arginine-glycine-aspartate (RGD)-dependent manner in human pancreatic carcinoma cells (Sheppard et al, 1990). The $\beta6$ subunit is composed of 788 amino acids and shares 34-51% sequence homology with other integrin subunits $\beta1-\beta5$. The $\beta6$ subunit also contains 9 potential glycosylation sites on the extracellular domain (Sheppard et al, 1990). The cytoplasmic domain differs from other subunits in that it is composed of a 41 amino acid region that is highly conserved among integrin subunits, and a unique 11 amino acid carboxy-terminal extension. The 11 amino acid extension has been shown not to be necessary for localisation of $\beta6$ to focal contacts. In fact, its removal appears to increase receptor localisation. However, removal of any of the three conserved regions identified as important for the localisation of $\beta1$ integrins to focal contacts (Reszka et al, 1992) has been shown to eliminate recruitment of $\beta6$ to focal contacts (Cone et al, 1994).

The integrin $\alpha v\beta6$ has previously been shown to enhance growth of colon cancer cells in vitro and in vivo, and this growth-enhancing effect is due, at least in part, to $\alpha v\beta6$ mediated gelatinase B secretion (Agrez et al, 1999). What has made this epithelial-restricted integrin of particular interest in cancer is that it is either not expressed or expressed at very low levels on normal epithelial cells, but is highly expressed during wound healing and tumourigenesis, particularly at the invading edge of tumour cell islands (Breuss et al, 1995; Agrez et al, 1996).

Integrins can signal through the cell membrane in either direction. The extracellular binding activity of integrins can be regulated from the cell interior as, for example, by phosphorylation of integrin cytoplasmic domains (inside-out signalling), while the binding of the extracellular matrix (ECM) elicits signals that are transmitted into the cell (outside-in signalling) (Gianotti and Ruoslahti, 1999). Outside-in signalling can be roughly divided into two descriptive categories. The first is 'direct signalling' in which ligation and clustering of integrins is the only extracellular stimulus. Thus, adhesion to ECM proteins can activate cytoplasmic tyrosine kinases (eg. focal adhesion kinase FAK) and serinethreonine kinases (such as those in the mitogen-activated protein kinase (MAPK) cascade) and stimulate lipid metabolism (eg. phosphatidylinositol-4,5-biphosphate $(P_1P_2)$ synthesis). The second category of integrin signalling is 'collaborative signalling', in which integrin-mediated cell adhesion modulates signalling events initiated through other types of receptors, particularly receptor tyrosine kinases that are activated by polypeptide growth factors (Howe et al, 1998). In all cases, however, integrin-mediated adhesion seems to be required for efficient transduction of signals into the cytosol or nucleus.

MAP kinases behave as a convergence point for diverse receptor-initiated signalling events at the plasma membrane. The core unit of MAP kinase pathways is a three-member protein kinase cascade in which MAP kinases are phosphorylated by MAP kinase kinases (MEKs) which are in turn phosphorylated by MAP kinase kinase kinases (e.g. Raf-1) (Garrington and Johnson, 1999). Amongst the 12 member proteins of the MAP kinase family are the extracellular signal-regulated kinases (ERKs) (Boulton et al, 1991) activated by phosphorylation of tyrosine and threonine residues which is the type of activation common to all known MAP kinase isoforms. ERK 1/2 (44 kD and 42 kD MAPks, respectively) share 90% amino acid identity and are ubiquitous components of signal transduction pathways (Boulton et al, 1991). These serine/threonine kinases phosphorylate and modulate the function of many proteins with regulatory functions including other protein kinases (such as $p90^{rsk}$) cytoskeletal proteins (such as microtubule-associated phospholipase $A_2$), upstream regulators (such as the epidermal growth factor receptor and Ras exchange factor) and transcription factors (such as c-myc and Elk-1). ERKs play a major role in growth-promoting events, especially when the concentration of growth factors available to a cell is limited (Giancotti and Ruoslahti, 1999).

Recently, MAP kinases have been found to associate directly with the cytoplasmic domain of integrins, and the binding domains of β3, β5 and β6 for ERK2 have been characterised (see International Patent Application No. WO 01/000677 and International Patent Application No. WO 02/051993). Those patent applications also showed that the cellular activity of cancer cells expressing β6 can be modulated by inhibiting binding of the MAP kinase with the integrin by treating the cells with peptides comprising the binding domain for the MAP kinase linked to the carrier peptide penetratin.

The distribution of β6 integrin subunit within various tissues has been assessed by both in situ hybridisation and immunostaining and reported in the art. For instance, β6 mRNA in adult primate tissues was detected only in epithelial cells and at very low or undetectable levels in most normal tissues (Breuss et al, 1993). High-level expression of β6 has been observed in secretory endometrial glands while low-level expression was detected in the ductal epithelia of salivary gland, mammary gland and epididymis, in gall and urinary bladder, and in the digestive tract.

Immunostaining data have also shown that β6 expression is restricted to epithelia and is up-regulated in parallel with morphogenetic events, tumourigenesis and epithelial repair (Breuss et al, 1993; 1995). During development of the kidney, lung and skin, β6 is expressed by specific types of epithelial cells, whereas it is mostly undetectable in normal adult kidney, lung and skin. In contrast, high level expression of β6 has been observed in several types of carcinoma. For example, β6 is almost invariably neo-expressed in squamous cell carcinomas derived from the oral mucosa, and often focally localised at the infiltrating edges of tumour cell islands (Breuss et al, 1995). Moreover, expression of the β6 subunit has been observed in renal cell carcinoma and testicular tumour cell lines (Takiuchi et al, 1994) and 50% of lung cancers have been shown to express this subunit (Smythe et al, 1995).

Recent studies have also shown that αvβ6 is a major fibronectin-binding receptor in colorectal cancer (Agrez et al, 1996). In addition, normal colonic epithelium from cancer patients does not express αvβ6 in immunostaining studies, and as with squamous cell carcinomas from the oral mucosa (Thomas et al, 1997), maximal β6 expression in colon cancer has been observed at the invading edges of tumour cell islands (Agrez et al, 1996).

Indeed, the β6 subunit is widely observed in cancers of various origins (Breuss et al, 1995). For example, β6 is detected in at least 50% of bowel cancer tumours. Others have reported its presence in oropharyngeal cancers where it is also present and strongly expressed in the invading margins of the cancer cell islands as is commonly found in bowel cancer. In the oropharyngeal mucosa, no β6 is observed in the normal lining cells of the mouth but in both primary and metastatic tumours from the oropharyngeal mucosa, strong β6 expression is seen which does not correlate with degree of differentiation and in particular, is restricted to the basal layer of epithelial cells.

Expression of β6 is also up-regulated in migrating keratinocytes at the wound edge during experimental epidermal wound healing. αvβ6 is not expressed in normal epithelium (Jones et al, 1997). However, following experimental wounding, αv appears to switch its heterodimeric association from β5 to β6 subunit during re-epithelialisation. At day 3 after wounding, β6 is absent but then appears around the perimeter of the basal cells of the migrating epidermis.

In human mucosal wounds, maximal expression of β6 has been observed relatively late when epithelial sheets are fused and granulation tissue is present (Haapasalmi et al, 1996). Furthermore, those investigators observed maximal expression of tenascin with αvβ6 expression. Interestingly, freshly isolated keratinocytes have not been found to express β6 but begin to express this after subculturing. In contrast to persistent αvβ6 expression observed in colon cancer cells, new expression of αvβ6 in migrating keratinocytes is down-regulated to undetectable levels once re-epithelialisation is complete. However in normal unwounded skin, just as in other normal epithelia, αvβ6 expression is absent indicating that this MAP kinase activation pathway is normally suppressed.

SUMMARY OF THE INVENTION

The present invention relates to the observation that the cellular activity of at least some types of cancer cells can be inhibited using an agent which binds to a binding domain of a MAP kinase for an integrin regardless of whether the integrin is expressed by the cells or not. It has also been found that some cancer cells may be substantially more susceptible to treatment with such an agent than corresponding normal cells. The reason for this is not known but this remarkable observation allows for essentially selective treatment of such cancers. In addition, the present invention in another form relates to the prophylaxis or treatment of cancers utilising agents which inhibit MAP kinase-integrin binding interactions, such as blood cell cancers.

Accordingly, in one aspect of the present invention there is provided a method for prophylaxis or treatment of a cancer in a mammal, the method comprising treating the mammal with an effective amount of an agent that binds to a MAP kinase such that binding of the MAP kinase to an integrin is inhibited, wherein the integrin is essentially not expressed by the cancer cells.

Typically, the agent will bind to a binding domain of the MAP kinase for the integrin. In a particularly preferred embodiment, the cancer will comprise a circulating blood cell cancer.

Hence, in a further aspect of the present invention there is provided a method for prophylaxis or treatment of a circulating blood cell cancer in a mammal, the method comprising treating the mammal with an effective amount of an agent that binds to a MAP kinase or integrin such that capacity of the MAP kinase to bind to the integrin is inhibited.

In another aspect of the present invention there is provided a method for prophylaxis or treatment of a cancer in a mammal, the method comprising subcutaneously administering to the mammal an effective amount of an agent for contact with cancer cells of the cancer at a site remote from the site of administration of the agent, wherein the agent binds to a MAP kinase or an integrin such that binding of the MAP kinase to the integrin is inhibited.

Typically, an agent utilised in a method of the invention will be adapted for passage across the outer cell membrane into the cancer cells of the cancer. Preferably, the agent will incorporate a facilitator moiety for facilitating passage of the polypeptide across the cell membrane of the cancer cells. The facilitator moiety will preferably be a signal peptide. The signal peptide will generally be a signal peptide for a growth factor and most preferably, a signal peptide for Kaposi fibroblast growth factor (K-FGF). Usually, the signal peptide will comprise or consist of the amino acid sequence AAVALLPAVLLALLA (SEQ ID No: 1), or a homologue, analogue, variant or derivative thereof.

It has also unexpectedly been found that greater inhibition of cancer cell activity can be achieved with a signal peptide having or incorporating the amino acid sequence AAVALLPAVLLALLA (SEQ ID No: 1) compared to other carrier moieties such as penetratin or for instance the β3 signal peptide VTVLALGALAGVGVG (SEQ ID No: 2). Preferably, the signal peptide will have the amino acid sequence AAVALLPAVLLALLAP (SEQ ID No: 3). It is believed the greater degree of inhibition of cellular activity observed is due to the greater capacity of the signal peptide to translocate across the outer cellular membrane. This is surprising as it was expected that a signal peptide for an integrin subunit chain would be more effective.

Accordingly, in another aspect of the present invention there is provided a method for prophylaxis or treatment of a cancer in a mammal, the method comprising administering to the mammal an effective amount of an agent incorporating a binding moiety which binds to a MAP kinase or an integrin such that binding of the MAP kinase to the integrin is inhibited, and a signal peptide having the amino acid sequence AAVALLPAVLLALLA (SEQ ID No: 1) for facilitating passage of the binding moiety into cancer cells of the cancer, or a homologue, analogue, variant or derivative of the signal peptide, which facilitates the passage of the binding moiety into the cancer cells.

In a further aspect of the present invention there is provided an agent for prophylaxis or treatment of a cancer in a mammal, the agent comprising a binding moiety which binds to a MAP kinase or an integrin such that binding of the MAP kinase to the integrin is inhibited, and a signal peptide having the amino acid sequence AAVALLPAVLLALLA (SEQ ID No: 1) for facilitating passage of the binding moiety into cancer cells of the cancer, or a homologue, analogue, variant or derivative of the signal peptide.

Preferably, the agent utilised in a method of the invention will be a polypeptide. The polypeptide may for example be a fusion protein. Preferably, the polypeptide will comprise the binding domain of the integrin to which the MAP kinase binds. In the instance not all the amino acids in the binding domain are involved in the binding interaction with the MAP kinase, the polypeptide may comprise only those amino acids of the binding domain which are directly involved in the binding interaction.

Preferably, the polypeptide will comprise the amino acid sequence RSKAKWQTGTNPLYR (SEQ ID No: 4), RARAKWDTANNPLYK (SEQ ID No: 5), or RSRARYEMASNPLYR (SEQ ID No: 6). Most preferably, the polypeptide will comprise an amino acid sequence selected from RSKAKNPLYR (SEQ ID No: 7), RARAKNPLYK (SEQ ID No: 8) and RSRARNPLYR (SEQ ID No: 9). Surprisingly, it has also been found that the amino acid sequence KEKLKNPLFK (SEQ ID No: 10) derived from the sequence KEKLKSQWNNDNPLFK (SEQ ID No: 11) of the cytoplasmic domain of the β2 integrin subunit can bind to a MAP kinase.

Hence, in another aspect of the present invention there is provided a method for prophylaxis or treatment of a cancer in a mammal, the method comprising treating the mammal with an effective amount of an agent that binds to a MAP kinase or integrin comprising β2, such that binding of the MAP kinase to the integrin is inhibited.

In still another aspect of the present invention there is provided an agent for modulating activity of cancer cells, the agent comprising a polypeptide having the sequence KEKLKSQWNNDNPLFK (SEQ ID No: 11) or KEKLKNPLFK (SEQ ID No: 10), or a homologue, analogue, variant or derivative thereof.

There are also provided nucleic acid sequences encoding polypeptides, homologues, analogues, and variants of the invention, recombinant vectors incorporating the nucleic acid sequences, and host cells transfected with such vectors. The vectors may for instance be cloning vectors, or expression vectors for expression of the polypeptides. The invention further extends to pharmaceutical compositions comprising at least one agent of the invention together with a pharmaceutically acceptable carrier. In addition, the present invention relates to the use of the agents of the invention, including nucleic acids and vectors incorporating them, in the manufacture of medicaments for the prophylaxis or treatment of cancer.

Rather than administering a polypeptide or fusion protein to a mammal in accordance with the invention, a nucleic acid molecule encoding the polypeptide or fusion protein, or a homologue or variant thereof, may be administered for expression of the polypeptide or fusion protein within the cancer cells. The nucleic acid sequence can be introduced into the cells in an appropriate expression vector for expression of the nucleic acid sequence extrachromosomally or more preferably, for integration of the nucleic acid sequence into genomic DNA by recombination events prior to expression of the polypeptide. Alternatively, the cells may be transfected with a nucleic acid molecule incorporating nucleotide sequences flanking the sequence encoding the polypeptide or fusion protein which facilitate recombination with genomic DNA for expression of the polypeptide under the control of the transfected cell's own transcriptional regulatory sequences.

Preferably, the integrin will be a member of the αV integrin subfamily. More preferably, the integrin is or incorporates an integrin subunit selected from the group consisting of β2, β3, β5, and β6.

Preferably, the MAP kinase will be selected from the group consisting of an extracellular signal-regulated kinase (ERK), a JNK MAP kinase, and a p38 MAP kinase. Preferably, the MAP kinase is ERK1, ERK2 or JNK-1. Most preferably, the MAP kinase is ERK2.

By "cancer" is meant any type of unregulated cell proliferation. The cancer may for instance be selected from the group consisting of an epithelial cell cancer, prostate cancer, a lymphoma or blood cell cancers and other cancers, including leukemias such as myeloid leukemias, eosinophilic leukemias and granulocytic leukemias. Where the cancer is a blood cell cancer, the agent with which the mammal is treated may bind to an integrin expressed by the blood cells of the cancer or to the MAP kinase such that binding of the MAP kinase with the integrin is thereby blocked or downregulated. Typically, the agent will bind to the binding domain of the integrin for the MAP kinase or to the binding domain of the MAP kinase that binds to the integrin. In the instance the agent binds to the integrin, the agent will usually be a fragment of the MAP kinase comprising the binding domain for the integrin, or a homologue, variant, analogue or derivative of such a fragment. Again, in the instance not all amino acids in the binding domain participate in the binding interaction, the agent may comprise only those amino acids of the binding domain which are directly involved in the binding interaction. The integrin may for example comprise β2 the expression of which is restricted to white blood cells (Hines et al, 1992).

Suitable fragments of MAP kinases capable of binding with an integrin are described in International Patent Application No. WO 02/051993 and include the amino acid sequences HRDLKPSNLLLNTTCDLKICDFGLAR (SEQ ID No: 12) and PSNLLLNTTCDLKIC (SEQ ID No: 13), and regions of such sequences.

The mammal may be any mammal treatable with a method of the invention. For instance, the mammal may be a member of the bovine, porcine, ovine or equine families, a laboratory test animal such as a mouse, rabbit, guinea pig, a cat or dog, or a primate or human being. Typically, the mammal will be a human being.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed anywhere before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the nature of the present invention may be more clearly understood, preferred forms thereof will now be described with reference to the following non-limiting examples.

BRIEF DESCRIPTION OF THE FIGURES

FIGS. 12A, 12B, 12C, 12D, and 12E show FACScan analysis results for normal human umbilical vein endothelial cells (HUVEC);

FIGS. 12F, 12G, and 12H show FACScan analysis results for SH-SY5Y neuroblastoma cells;

FIGS. 12I, 12J, and 12K show FACScan analysis results for HL60 leukemia cells;

FIGS. 12L, 12M, and 12N show FACScan analysis results for DU 145 prostate cancer cells;

FIGS. 23A, 23B, 23C, 23D, 23E, 23F, 23G, and 23H are FACScan results showing essentially selective killing of HT29 colon cancer cells by the peptide AAVALLPAVL-LALLARSKAKNPLYR (SEQ ID No: 17) relative to normal cells.

DETAILED DESCRIPTION OF PREFERRED EMBODIMENTS OF THE INVENTION

Figure 1:
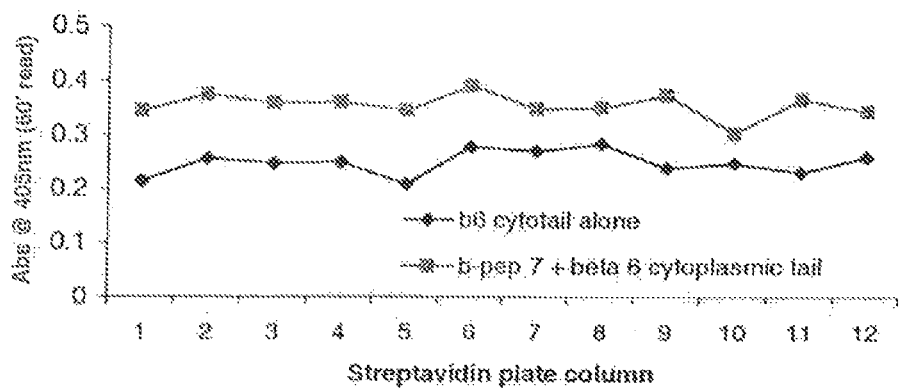
FIG. 1 is a graph showing the binding of an ERK2 fragment to the cytoplasmic domain of β6.

In the broadest sense, the term "integrin" unless otherwise specified, is to be taken to encompass an integrin family member or integrin subunit, or a homologue, derivative, variant or analogue of an integrin subunit, or an integrin family member incorporating at least one such homologue, derivative, variant or analogue of an integrin subunit.

By "binding domain" is meant the minimum length of contiguous amino acid sequence of the MAP kinase or integrin required for binding of the integrin or MAP kinase, respectively.

The term "homologue" is to be taken to mean a molecule that has amino acid sequence similarity. The homology between amino acid sequences is determined by comparing amino acids at each position in the sequences when optimally aligned for the purpose of comparison. The sequences are considered homologous at a position if the amino acids at that position are the same. Typically, a homologue will have an overall amino acid sequence homology of at least about 50% or 70% and most preferably, greater than about 80%, 90% or 98% sequence homology. Homology with a binding domain may be greater than the overall amino acid sequence homology of the homologue and will usually be greater than about 80% and preferably, greater than about 90%, 95% or 98%.

A homologue may be provided by, or the result of, the addition of one or more amino acids to an amino acid sequence, deletion of one or more amino acids from an amino acid sequence and/or the substitution of one or more amino acids with another amino acid or amino acids. Inversion of amino acids and other mutational changes that result in alteration of an amino acid sequence are also encompassed. A homologue may be prepared by introducing nucleotide changes in a nucleic acid sequence such that the desired amino acid changes are achieved upon expression of the mutagenised nucleic acid or for instance, by synthesising an amino acid sequence incorporating the desired amino acid changes.

The substitution of an amino acid may involve a conservative or non-conservative amino acid substitution. By conservative amino acid substitution is meant replacing an amino acid residue with another amino acid having similar stereochemical properties which does not substantially affect the conformation or the desired aspect or aspects of characteristic biological function. Preferred homologues include ones having amino acid sequences in which one or more amino acids have been substituted with alanine or other neutrally charged amino acid residue(s), or to which one or more such amino acid residues have been added. A homologue may also incorporate an amino acid or amino acids not encoded by the genetic code. For example, D-amino acids rather than L-amino acids may be utilised. A proteinaceous agent of the invention may for instance consist wholly or only partially of L- or D-amino acids.

By the term "variant" is meant an isoform of a polypeptide or fragment thereof, a naturally occurring mutant form of a polypeptide or fragment thereof, or a polypeptide or fragment thereof encoded by an allelic variant or partial nucleic acid sequence thereof.

The term "analogue" encompasses a molecule that differs from the original molecule but retains similarity in one or more features that provide the biological function characteristic of the original molecule. An analogue may have substantial overall structural similarity with the original molecule or only structural similarity with one or more regions of the original molecule responsible for the desired characteristic biological function. By "structural" similarity it is meant similarly in shape, conformation and/or other structural features responsible for the provision of the biological function or which otherwise have involvement in the provision of the biological function. Alternatively, it will be understood that with knowledge of the region(s) or domain(s) of a molecule having the desired characteristic biological function or knowledge of a binding domain to which the molecule binds, analogues may be provided that while differing in structure or chemical groups nevertheless possess such biological function. Indeed, an analogue may be a mimetic such as a peptido-mimetic. However, it is not necessary that an analogue have amino acid sequence homology, and an analogue may not be proteinaceous at all.

By the term "derivative" is meant a molecule that is derived or obtained from the original molecule and which retains one or more aspects or characteristic biological function of that molecule. A derivative may for instance be provided as a result of the cleavage of the original molecule, cyclisation and/or coupling with one or more additional moieties that improve solubility, lipophilic characteristics to enhance uptake by cells, stability or biological half-life, increased cellular toxicity, or for instance to act as a label for subsequent detection or the like. A derivative may also result from post-translational or post-synthesis modification such as the attachment of carbohydrate moieties, or chemical reaction(s) resulting in structural modification(s) such as the alkylation or acetylation of amino acid residues or other changes involving the formation of chemical bonds.

The term "polypeptide" is used interchangeably herein with "peptide" and encompasses amino acid sequences incorporating only a few amino acid residues or many amino acid residues coupled by peptide bonds. For instance, it will be understood that agents such as RSKAKNPLYR (SEQ ID No: 7) and KEKLKNPLFK (SEQ ID No: 10) fall within the scope of the term.

Typically, a polypeptide of the invention or administered to a mammal in accordance with the invention will have a length of about 150 amino acids or less, more preferably about 75 amino or 50 amino acids or less and most preferably, about 40 amino acids or less. When the polypeptide is a fusion protein or agent incorporating a carrier moiety, the binding moiety that binds to the integrin will generally have a length of between about 5 to about 50 amino acids and more preferably, a length of between about 5 to about 35 amino acids.

The binding domain of an integrin to which a MAP kinase binds or the binding domain of the MAP kinase for the integrin may be identified and characterised using protocols and techniques described in International Patent Application No. WO 01000677 and International Patent Application No. WO 02051993, the disclosures of both of which are expressly incorporated herein by reference in their entirety.

More specifically, a binding domain may be localised by assessing the capacity of respective overlapping peptide fragments of the cytoplasmic domain of an integrin subunit or from a MAP kinase to bind with the MAP kinase or integrin, respectively. The specific amino acid sequence which constitutes the binding domain may then be determined utilising progressively smaller peptide fragments. In particular, test peptides are readily synthesised to a desired length involving deletion of an amino acid or amino acids from one or both of the N-terminal and C-terminal ends of the larger amino acid sequence, and tested for their ability to bind with the MAP kinase or the integrin. This process is repeated until the minimum length peptide capable of binding with the MAP kinase or the integrin substantially without compromising the optimum observed level of binding is identified.

The identification of amino acids that play an active role in the MAP kinase integrin interaction may be achieved with the use of further synthesised test peptides in which one or more amino acids of the sequence are deleted or substituted with a different amino acid or amino acids to determine the effect on the ability of the peptide to bind with the MAP kinase or the integrin. By deletion in this context is meant deletion of one or more of the amino acids between the N-terminal and C-terminal amino acid residues of the identified binding domain. Typically, substitution mutagenesis will involve substitution of selected ones of the amino acid sequence with alanine or other relatively neutrally charged amino acid.

Nucleotide and amino acid sequence data for the β6 integrin subunit for instance is found in Sheppard et al, 1990. The nucleotide and amino acid sequence for ERK2 may be found in Boulton et al, 1991. Reference to such published data allows the ready design of peptide fragments of an integrin subunit cytoplasmic domain for use in the identification and localisation of the binding domain of the integrin for the MAP kinase, and the identification of corresponding nucleic acid sequences encoding the peptide fragments.

Localisation and characterisation of a binding domain of an integrin for a MAP kinase enables the design of agents which bind to the binding domain for modulation of cell activity. This will typically involve determining the physical properties of the binding domain such as size and charge distribution, and the tertiary structure of the binding domain. Specifically, at least the region of the integrin or MAP kinase containing the binding domain is modelled taking into account the stereochemistry and physical properties of the binding domain such as size and charge distribution as well as its three dimensional structure as determined using x-ray crystallography, nuclear magnetic resonance and/or commercially available computer modelling software. Such modelling techniques are well known in the art. In a variation of this approach, the modelling will take into account the binding interaction of the binding domain with the MAP kinase or the integrin such that any change in conformation arising from the interaction may be taken in to account in the design of an analogue. Modelling flanking regions adjacent the binding domain also allows the design of agents for binding with such flanking regions but which are nevertheless capable of inhibiting the MAP kinase integrin interaction either by stearic hindrance or by distorting the conformation of the binding domain of the MAP kinase or integrin (eg. allostearic inhibitors).

The design of an analogue will usually involve selecting or deriving a template molecule onto which chemical groups are grafted to provide required physical and chemical characteristics or for further chemical reactions for achieving the required physical and chemical characteristics. The selection of template molecule and chemical groups is based on ease of synthesis, likely pharmacological acceptability, risk of or potential for degradation in vivo, stability and maintenance of biological activity upon administration.

In order to constrain a polypeptide or other agent in a three dimensional conformation required for binding, it may be synthesised with side chain structures or be synthesised incorporating cysteine residues which form a disulfide bridge, or otherwise be incorporated into a molecule with a known stable structure in vivo. For example, a polypeptide or the like may be incorporated into an amino acid sequence at least part of which folds into a β-pleated sheet or helical structure such as an α-helix.

A polypeptide or other agent may also be cyclised to provide enhanced rigidity and thereby stability in vivo. Various methods for cyclising peptides, fusion proteins or the like are known (eg. Schiller et al., 1985). For example, a synthetic peptide incorporating two cysteine residues distanced from each other along the peptide may be cyclised by the oxidation of the thiol groups of the residues to form a disulfide bridge between them. Cyclisation may also be achieved by the formation of a peptide bond between the N-terminal and C-terminal amino acids of a synthetic peptide or for instance through the formation of a bond between the positively charged amino group on the side chain of a lysine residue and the negatively charged carboxyl group on the side chain of a glutamine acid residue. As will be understood, the position of the various amino acid residues between which such bonds are formed will determine the size of the cycle. Variation of cycle size for optimisation of binding affinity may be achieved by synthesising peptides in which the position of amino acids for achieving cyclisation has been altered. The formation of direct chemical bonds between amino acids or the use of any suitable linker to achieve a desired three-dimensional conformation is also well within the scope of the skilled addressee.

Strategies for identifying agents suitable for use in methods of the present invention include large scale screening techniques. For example, peptide library protocols provide an efficient way of testing a vast number of potential agents. Such libraries and their use are well known. Prospective agents identified may be then further evaluated in suitable activity, competitive and other assays. A method of screening for an agent or evaluating whether an agent is capable of binding to the binding domain of an integrin for a MAP kinase and thereby inhibiting the MAP kinase integrin interaction, may for instance involve utilising the agent in an assay whereby the agent has the opportunity of binding to the MAP kinase in the presence of the integrin prior to the addition of the integrin, and determining whether inhibition of binding of the MAP kinase to the integrin results. An alternate screening method may for instance involve selecting a test agent and measuring cellular activity of target cells in the presence of the test agent, and comparing that activity with cellular activity in the absence of the test agent. Cellular activity may be assessed by cell growth as indicated by [$^3$H]-thymidine uptake or other measurement of cellular activity. As will be understood, a difference in observed functional activity in the presence of the test agent is indicative of the modulating effect provided by the test agent.

It will be understood that the integrin in the context of such assays may be an integrin subunit or polypeptide or fragment incorporating the binding domain of the integrin to which the MAP kinase binds, or a homologue, analogue, variant or derivative of such a molecule to which the MAP kinase is capable of binding. Similarly, a MAP kinase in this context may be an intact MAP kinase or a fragment thereof incorporating a binding domain for the integrin, or a homologue, analogue, variant or derivative thereof that is capable of binding with the integrin.

Determination of whether an agent is capable of binding to the binding domain of the MAP kinase or integrin may be achieved using a polypeptide or fragment as described herein consisting of the binding domain of the integrin or MAP kinase or the binding sequence or fragment thereof of the binding domain that directly participates in the binding interaction, or analogs or the like of such molecules.

In this regard, the regions or amino acids in the binding domain that participate in the binding interaction may be separated by amino acids that are not involved in the binding interaction. The binding sequence of a binding domain is the sequence of amino acids which participate in the binding interaction excluding those amino acids in the binding domain that do not participate in the binding interaction. As an example, the binding domain of β6 comprises the amino acid sequence RSKAKWQTGTNPLYR (SEQ ID No: 4). However, the intervening amino acid sequence WQTGT (SEQ ID No: 20) does not directly participate in binding with the MAP kinase ERK2. That is, even if the sequence WQTGT (SEQ ID No: 20) is deleted, a peptide with the amino acid sequence RSKAKNPLYR (SEQ ID No: 7) is still bound by ERK2. Similarly, the binding domains of β3 and β5 for ERK2 comprise RARAKWDTANNPLYK (SEQ ID No: 8) and RSRARYEMASNPLYR (SEQ ID No: 6), respectively. Deletion of the intervening sequences WDTAN (SEQ ID No: 21) and YEMAS (SEQ ID No: 22) from the sequences yields the peptides RARAKNPLYK (SEQ ID No: 8) and RSRARNPLYR (SEQ ID No: 9) both of which are still bound by ERK2.

Alignment of binding domains of β2, β3 and β5 and β6 results in the concensus scheme R/K x R/K * R/K - xx*x* NPL Y/F R/K wherein R/K is either arginine or lysine, Y/F is either tyrosine or phenylalanine, x may be any amino acid, * is a hydrophobic amino acid residue, and—is an amino acid (serine) present in the binding domain of β2 but not in the others and which may be replaced with another amino acid such as threonine, tyrosine, asparagine or glutamine, or be deleted. Accordingly, peptides are provided that comprise or consist of this sequence that may find application in methods of the invention. As indicated above, the intervening amino acid sequence indicated by —xx*x* may also be deleted such that an agent of the invention comprising or consisting of the sequence RKxRK*RKNPLYFRK is provided.

A particularly preferred way of achieving intracellular delivery of polypeptides, nucleic acids and other agents is to use a "facilitator molecule" such as a carrier peptide, which has the ability to deliver cargo macro-molecules across cell membranes in an energy-independent manner. Such carrier peptides provide the possibility of both testing potential agents in cell culture without drastically altering cell membrane integrity and of delivering agents in vivo. Carrier peptides that are known in the art include penetratins and variants thereof (Derossi et al, 1994, 1996), human immunodeficiency virus Tat derived peptide (Prociantz, 1996), transportan derived peptide (Pooga et al, 1998) and signal peptides.

Particularly preferred signal peptides are described in U.S. Pat. No. 5,807,746 the contents of which are incorporated herein in its entirety. In particular, a signal peptide for Kaposi fibroblast growth factor (K-FGF) having or incorporating the amino acid sequence AAVALLPAVLLALLA (SEQ ID No: 1) or AAVALLPAVLLALLAP (SEQ ID No: 3) is preferred.

It is not necessary that a signal peptide used in a method of the invention be a complete signal peptide and fragments or homologues and the like which retain the ability to penetrate the outer cellular membrane to effect delivery of the attached agent into the cytosol of the cell may be utilised. In the instance the agent is a nucleic acid, the signal peptide will typically also be capable of penetrating through the nuclear membrane of eukaryotic cells and thereby effecting translocation of the attached nucleic acid into the nucleus of the cell.

Rather than a carrier peptide, the facilitator molecule may comprise a lipid moiety or other non-peptide moiety which enhances cell membranes solubility of the agent selected for binding to the MAP kinase or integrin, such that passage of the agent across the cell membrane is facilitated. The lipid moiety may for instance be selected from triglycerides including mixed triglycerides. Fatty acids are preferred and particularly, $C_{16}$-$C_{20}$ fatty acids. Typically, the fatty acid will be a saturated fatty acid and most preferably, a stearic acid.

The invention is not limited to the use of any such non-peptide facilitator molecule, and any molecule which provides the desired cell membrane solubility that is physiologically acceptable may be used.

The agent may be linked to the facilitator molecule in any conventionally known manner. For instance, a polypeptide may be linked directly to a carrier peptide through an amino acid linker sequence by a peptide bond or non-peptide covalent bond using a crosslinking reagent. For agents that have a negative charge such as nucleic acids, the agent may be linked to the carrier peptide by charge-association between the negatively charged agent and the positively charged amino acids in the carrier peptide or linker sequence. Chemical ligation methods may also be used to create a covalent bond between the carboxy terminal amino acid of the carrier peptide or linker sequence and the agent.

Specific targeting of agents to abnormal cells can be realised by coupling a ligand or antibody or binding fragment thereof (such as Fab and F(ab)$_2$ fragments) to facilitator molecules such as penetratin for facilitating passage across the outer cell membrane of cancer cells, which are in turn coupled to the agent. Another approach may employ coupling the carrier-agent complex to integrin receptor-targeted peptides which target an extracellular integrin domain. For example, peptides with the sequence DLXXL (SEQ ID No: 23) can be used to target the extracellular domain of β6. Given that β6 expression enhances effective proteolysis at the cell surface by matrix metalloproteinase-9 (MMP-9) (Agrez et al, 1999), such targeting approaches include engineering an MMP-9 cleavage site between the targeting moiety and the carrier to facilitate internalisation of the carrier-agent complex. As another example, the ligand recognition motif for αVβ6 integrin, RTDLDSLRTYTL (SEQ ID No: 24) may be used in conjunction with or without an engineered MMP-9 cleavage site to deliver the carrier-agent complex to the surface of the target cell. Further protocols for delivering nucleic acids to cells by targeting integrins is described in Bachmann et al, 1998.

The provision of fusion proteins and use of fusion proteins incorporating a polypeptide which binds to the binding domain of a MAP kinase for an integrin is expressly provided for by the invention. Polypeptides and fusion proteins or the like may be synthesised or produced using conventional recombinant techniques. Nucleic acid encoding a fusion protein may for instance be provided by joining separate DNA fragments encoding peptides or polypeptides having desired three dimensional conformations and/or amino acid sequences by employing blunt-ended termini and oligonucleotide linkers, digestion to provide staggered termini as appropriate, and ligation of cohesive ends. Alternatively, PCR amplification of DNA fragments can be utilised employing primers which give rise to amplicons with complementary termini which can be subsequently ligated together (eg. see Ausubel et al. (1994) Current Protocols in Molecular Biology, USA, Vol. 1 and 2, John Wiley & Sons, 1992; Sambrook et al (1998) Molecular cloning: A Laboratory Manual, Second Ed., Cold Spring Harbour Laboratory Press, New York).

Polypeptides and fusion proteins may be expressed in vitro and purified from cell culture for administration to a subject, or cells may be transfected with nucleic acid encoding a polypeptide or fusion protein for in vitro or in vivo expression thereof. The nucleic acid will typically first be introduced into a cloning vector and amplified in host cells, prior to the nucleic acid being excised and incorporated into a suitable expression vector for transfection of cells.

Typical cloning vectors incorporate an origin of replication (ori) for permitting efficient replication of the vector, a reporter or marker gene for enabling selection of host cells transformed with the vector, and restriction enzyme cleavage sites for facilitating the insertion and subsequent excision of the nucleic acid sequence of interest. Preferably, the cloning vector has a polylinker sequence incorporating an array of restriction sites. The marker gene may be drug-resistance gene (eg. Amp$^r$ for ampicillin resistance), a gene encoding an enzyme such as chloramphenicol acetyltransferase (CAT), β-lactamase, adenosine deaminase (ADA), aminoglycoside phosphotransferase (APH), dihydrofolate reductase (DHFR), hygromycin-B-phosphotransferase (HPH), thymidine kinase (TK), or for instance β-galactosidase encoded by the E. coli lacZ gene (LacZ'). Yeast reporter genes include imidazole glycerolphosphate dehydratase (HIS3), N-(5'-phosphoribosyl)-anthranilate isomerase (TRP1) and β-isopropylmalate dehydrogenase (LEU2). As will be appreciated, expression vectors of the invention may also incorporate such marker genes.

Cloning vectors include cloning vectors for mammalian, yeast and insect cells. Particular vectors that may find application include pBR322 based vectors and pUC vectors such as pUC118 and pUC119. Suitable expression and cloning vectors are for instance described in Molecular Cloning. A Laboratory Manual, Sambrook et al., 2nd Ed. Cold Spring Harbour Laboratory, 1989.

Suitable expression vectors include plasmids and cosmids capable of expression of a DNA (eg. genomic DNA or cDNA) insert. An expression vector will typically include transcriptional regulatory control sequences to which the inserted nucleic acid sequence is operably linked. By "operably linked" is meant the nucleic acid insert is linked to the transcriptional regulatory control sequences for permitting transcription of the inserted sequence without a shift in the reading frame of the insert. Such transcriptional regulatory control sequences include promoters for facilitating binding of RNA polymerase to initiate transcription, expression control elements for enabling binding of ribosomes to transcribed mRNA, and enhancers for modulating promoter activity. A promoter may be a tissue specific promoter which facilitates transcription of the nucleic acid insert only in specific cell lineages and not in other cell types or only to a relatively low level in such other cell types. The design of an expression vector will depend on the host cell to be transfected, the mode of transfection and the desired level of transcription of the nucleic acid insert.

Numerous expression vectors suitable for transfection of prokaryotic (eg. bacterial) or eukaryotic (eg. yeast, insect or mammalian cells) are known in the art. Expression vectors suitable for transfection of eukaryotic cells include pSV2neo, pEF.PGK.puro, pTk2, pRc/CNV, pcDNAI/neo, non-replicating adenoviral shuttle vectors incorporating the polyadenylation site and elongation factor 1-α promoter and pAdEasy based expression vectors most preferably incorporating a cytomegalovirus (CMV) promoter (eg. see He et al, 1998). For expression in insect cells, baculovirus expression vectors may be utilised examples of which include pVL based vectors such as pVL1392, and pVL941, and pAcUW based vectors such as pAcUW1. Viral expression vectors are preferred, and most preferably, adenovirus vectors will be utilised.

Any means for achieving the introduction of the nucleic acid into a target cell may be used. Transfer methods known in the art include viral and non-viral transfer methods. Suitable virus into which appropriate viral expression vectors may be packaged for delivery to target cells include adenovirus, vaccinia virus, retroviruses of avian, murine and human origin, herpes viruses including Herpes Simplex Virus (HSV) and EBV, papovaviruses such as SV40, and adeno-associated virus. Particularly preferred virus are replication deficient recombinant adenovirus (eg. He et al, 1998). Engineered virus may be administered locally or systemically to achieve delivery of nucleic acid sequence into a target cell.

Rather than utilising viral mediated transfection of cells, nucleic acid sequences and other agents may be introduced into a cell in vitro or in vivo by liposome mediated transfection. The liposomes may carry targeting molecules for maximising delivery of the agent or agents contained therein to specific cell types of interest. Such targeting molecules include antibodies or binding fragments thereof as described above, ligands or cell surface receptors for facilitating fusion of liposomes to the specific cells of interest. Agents may also be intracellularly delivered in vitro using conventional cold or heat shock techniques or for instance, calcium phosphate coprecipitation or electroporation protocols as are known in the art. Yet another strategy is to design the agent to have the inherent ability to pass across the lipid bilayer of a cell.

Host cells that may be used for expression of polypeptides or fusion proteins include bacteria such as *E. coli, Bacillus* such as *B. subtilis, Streptomyces* and *Pseudomonas* bacterial strains, yeast such as *Saccharomyces* and *Pichia*, insect cells, avian cells and mammalian cells such as Chinese Hamster Ovary cells (CHO), COS, HeLa, HaRas, WI38, SW480, and NIH3T3 cells. The host cells are cultured in a suitable culture medium under conditions for facilitating expression of the introduced nucleic acid prior to purification of the expressed product from the host cells, and/or supernatants as the case may be using standard purification techniques.

The toxicity profile of an agent may be tested on normal and abnormal cells such as cancer cells by evaluation of cell morphology, trypan-blue exclusion, assessment of apoptosis and cell proliferation studies (eg. cell counts, $^3$H-thymidine uptake and MTT assay).

The cancer treated by a method of the invention may for instance be selected from the group consisting of leukaemias, myeloid leukaemias, eosinophilic leukaemias, granulocytic leukaemias, and cancer of the liver, tongue, salivary glands, gums, floor and other areas of the mouth, oropharynx, nasopharynx, hypopharynx and other oral cavities, oesophagus, gastrointestinal tract, stomach, small intestine, duodenum, colon, rectum, gallbladder, pancreas, larynx, trachea, bronchus, lung, breast, uterus, cervix, ovary, vagina, vulva, prostate, testes, penis, bladder, kidney, thyroid, and skin. Typically, the cancer will be an epithelium cancer and most usually, a non-dermal cancer.

Agents of the invention may be co-administered with one or more other compounds or drugs. For example, an agent or agents may be co-administered in combination or in conjunction with antisense therapy or chemotherapeutic drugs. By "co-administered" is meant simultaneous administration in the same formulation or in two different formulations by the same or different routes, or sequential administration by the same or different routes. By "sequential" administration is meant one is administered after the other, typically with a time delay of from very short times up to hours or for instance days.

The agent or agents will typically be formulated into a pharmaceutical composition incorporating a pharmaceutically acceptable carriers and/or excipient for administration to the intended subject. Pharmaceutical compositions include sterile aqueous solutions suitable for injection, (where the agent or agents is water soluble) and sterile powders for the extemporaneous preparation of sterile injectable solutions. Such injectable compositions will be fluid to the extent that the syringability exists and typically, will be stable to allow for storage after manufacture. The carrier may be a solvent or dispersion medium containing one or more of ethanol, polyol (eg. glycerol, propylene glycol, liquid polyethylene glycol and the like), vegetable oils and mixtures thereof. Fluidity may be maintained by the use of a coating such as lecithin and by the use of surfactants.

Sterile injectable solutions will typically be prepared by incorporating the active agents in the desired amount in the selected solvent with various other components enumerated above, prior to sterilising the solution by filtration. Generally, dispersions will be prepared by incorporating the sterile active agents into a sterile vehicle which contains the dispersion medium and other components. In the case of sterile powders, preferred methods of preparation are vacuum drying and freeze-drying techniques which yield a powder of the active agent plus any additional desired ingredient from previously sterile filtered solutions thereof.

For oral administration, the active agents may be formulated into any orally acceptable carrier deemed suitable. In particular, the active ingredient may be formulated with an inert diluent, an assimilable edible carrier or it may be enclosed in a hard or soft shell gelatin capsule. Moreover, an active agent may be incorporated with excipients and used in the form of ingestable tablets, buccal tablets, troches, capsules, elixirs, suspensions or syrups.

Active agents may also be formulated into topically acceptable carriers conventionally used for forming creams, lotions or ointments for internal or external application. Topical formulations may be applied to a site to be treated by dressings and the like impregnated with the formulation.

Typically, a composition of the invention will incorporate one or more preservatives such as parabens, chlorobutanol, phenol, sorbic acid, and thimersal. In many cases, a composition may furthermore include isotonic agents such as sugars or sodium chloride. In addition, prolonged absorption of the composition may be brought about by the use in the compositions of agents for delaying absorption such as aluminium monosterate and gelatin.

Tablets, troches, pills, capsules and the like may also contain one or more of the following: a binder such as gum tragacanth, *acacia*, corn starch or gelatin; a disintegrating agent such as corn starch, potato starch or alginic acid; a lubricant such as magnesium sterate; a sweetening agent such as sucrose, lactose or saccharin; and a flavouring agent.

Pharmaceutically acceptable carriers include any suitable conventionally known solvents, dispersion media and isotonic preparations or solutions. Use of such ingredients and media for pharmaceutically active substances is well known. Except insofar as any conventional media or agent is incompatible with the active agent, use thereof in therapeutic and prophylactic compositions is included. Supplementary active ingredients can also be incorporated into the compositions if desired.

It is particularly preferred to formulate parenteral compositions in dosage unit form for ease of administration and uniformity of dosage. Dosage unit form as used herein is to be taken to mean physically discrete units suited as unitary dosages for the subject to be treated, each unit containing a predetermined quantity of active agent calculated to produce the desired therapeutic or prophylactic effect in association with the relevant carrier used.

When the dosage unit form is a capsule, it may contain in addition to one or more of the above ingredients a liquid carrier. Various other ingredients may be present as coatings or to otherwise modify the physical form of the dosage unit. For instance, tablets, pills or capsules may be coated with shellac, sugars or both. In addition, an active agent may be incorporated into any suitable sustained-release preparation or formulation.

Pharmaceutical compositions will generally contain at least about 1% by weight of the active agent or agents. The percentage may of course be varied and may conveniently be between about 5 to about 80% ww of the composition or preparation. As will be appreciated, the amount of active agent or agents in such compositions will be such that a suitable effective dosage will be delivered to the subject taking into account the proposed mode of administration. Preferred oral compositions according to the invention will contain between about 0.1 µg and 4000 mg of the active agent.

In addition, a pharmaceutical composition may contain a vector of the invention capable of transfecting target cells. The vector may for instance, be packaged into a suitable virus for delivery of the vector into target cells as described above.

The dosage of an active agent will depend on a number of factors including whether the agent is to be administered for prophylactic or therapeutic use, the condition for which the agent is intended to be administered, the severity of the condition, the age of the subject, and related factors including weight and general health of the subject as may be determined by the physician or attendant in accordance with accepted principles. For instance, a low dosage may initially be given which is subsequently increased at each administration following evaluation of the subject's response. Similarly, frequency of administration may be determined in the same way that is, by continuously monitoring the subject's response between each dosage and if necessary, increasing the frequency of administration or alternatively, reducing the frequency of administration. Typically, an agent will be administered in accordance with a method of the invention at a dosage up to about 50 mg/kg body weight of the mammal and preferably in a range of from about 20 mg/kg to 40 mg/kg body weight.

The route of administration of a pharmaceutical composition will again depend on the nature of the condition for which the composition is to be administered. Suitable routes of administration include but are not limited to respiritoraly, intratracheally, nasopharyngeally, intravenously, intraperitonealy, subcutaneously, intracraniatly, intradermally, intramuscularly, intraoccularly, intrathecally, intranasally, by infusion, orally, rectally, via IV group patch, topically and by implant. With respect to intravenous routes, particularly suitable routes are via injection into blood vessels which supply a tumour or particular organs to be treated. Agents may also be delivered into cavities such for example the pleural or peritoneal cavity, or be injected directly into tumour tissue. Subcutaneous administration of polypeptide agents is preferred. Suitable pharmaceutically acceptable carriers and formulations useful in compositions of the present invention may for instance be found in handbooks and texts well known to the skilled addressee, such as "Remington: The Science and Practice of Pharmacy (Mack Publishing Co., 1995)", the contents of which is incorporated herein in its entirety by reference.

The present invention will be described herein after with reference to a number of examples.

EXAMPLE 1

Binding of MAP Kinases to the Cytoplasmic Domain of Integrin Subunit Chains 1.1: ELISA Assay for Detection of MAP Kinase Binding An assay was developed for detecting the ability of MAP kinases to bind with a peptide agent in solution.

Briefly, the MAP kinase is added to an eppendorf tube containing a biotinylated test peptide in phosphate buffered saline (PBS) at pH 7.4. The mixture is allowed to stand at room temperature for 10 minutes with occasional mixing by gentle inversion of the tube. The MAP kinase/test peptide mixture is then transferred to a pre-washed (PBS×3×100 µl) 96-well streptavidin coated ELISA microtitre plate and allowed to stand for 60 minutes at room temperature. At the end of the 60 minute period, the MAP kinase/test peptide mixture is tipped from the ELISA plate and the wells washed 3 times with wash solution (PBS+0.05% Tween–20).

Primary antibody detection for the MAP kinase is then added to the test wells and the ELISA plate is allowed to stand for a further 30 minutes at room temperature before the antibody solution is decanted from the plate and the wells again washed with the wash solution. Optimal dilutions of primary detection antibody are pre-determined for each target MAP kinase. Alkaline-phosphatase or other enzyme conjugated anti-primary species antibody at a dilution of 1:2000 v/v is subsequently added to the wells and the microtitre plate is allowed to stand for another 30 minutes at room temperature, before the washing step is repeated and phosphatase detection reagent is added to the wells and the colour reaction allowed to develop. The wells are read at 405 nm using a microplate reader (Bio-Rad). Controls comprise non-biotinylated peptide and biotinylated peptide alone 1.2: ERK, JNK and p38 MAP Kinases Bind to Integrins The binding of various MAP kinases to the cytoplasmic domain of β6 was tested using the assay described in Example 1.1. Specifically, the biotinylated ERK2 amino acid sequence biotin-HRDLKPSNLLLNTTCDLKICDF-GLAR (SEQ ID No: 25) was incubated with the cytoplasmic domain of β6 having the amino acid sequence HDRKEV-AKFEAERSKAKWQTGTNPLYRGSTSTFKNV-TYKHREKQKVDLSTDC (SEQ ID No: 26), and the binding interaction detected using the anti-β6 antibody R6G9. The ERK fragment bound to the β6 domain is shown in FIG. 1.

Figure 2:
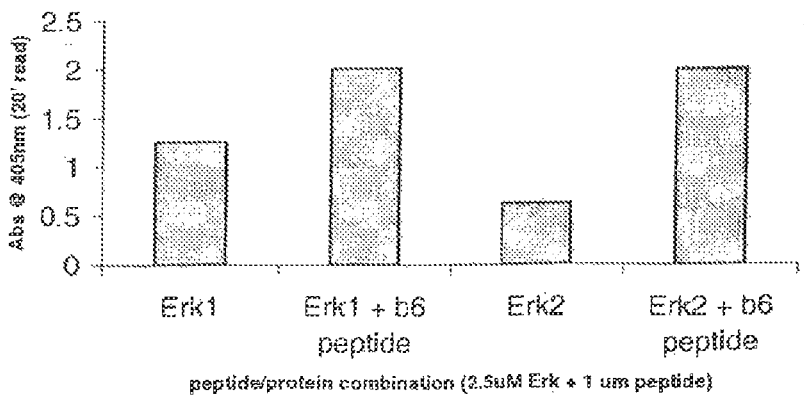
FIG. 2 is a graph showing the binding of the MAP kinases ERK1 and ERK2 to a fragment comprising the binding domain of β6.

Similarly, the binding of ERK1 and ERK2 to the fragment RSKAKWQTGTNPLYR (SEQ ID No: 4) comprising the binding domain of the β6 integrin subunit was tested using the assay of Example 1.1 and the results are shown in FIG. 2. As can be seen, both ERK1 and ERK2 bind to the β6 fragment. ERK1 and ERK2 used for all studies was obtained by purification of the protein following cleavage of GST-ERK1/2 with thrombin. GST-ERK1/2 are fusion proteins consisting of ERK coupled to glutathione-S-transferase and purified from host cells transfected with pGEX-4T vector.

Figure 3:
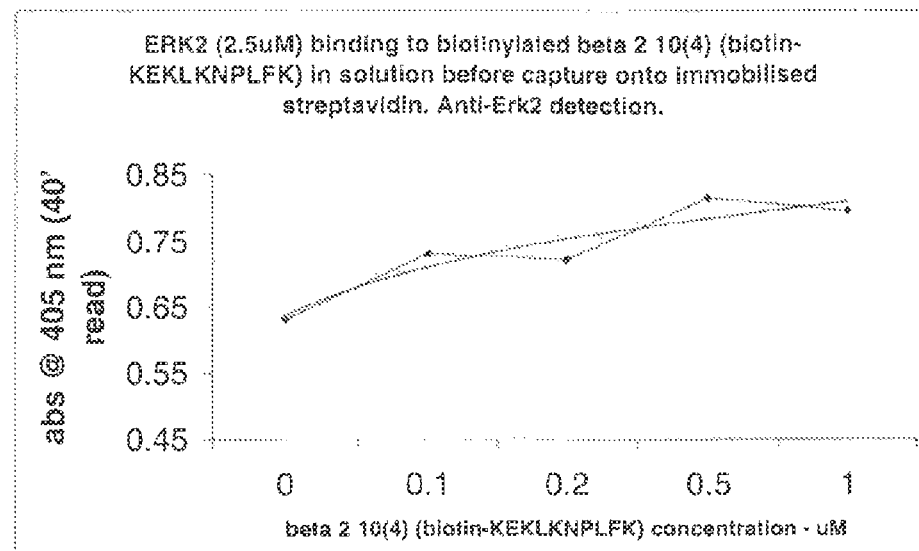
FIG. 3 is a graph showing the binding of ERK2 to the peptide KEKLKNPLFK (SEQ ID No: 10) comprising the binding sequence of β2.

The fragment of β2 corresponding to the amino acid sequence RSKAKWQTGTNPLYR (SEQ ID No: 4) of β6 is KEKLKSQWNNDNPLFK (SEQ ID No: 11). The peptide RSKAKNPLYR (SEQ ID No. 7) (arbitrarily designated peptide 10(4)) obtained by the deletion of the intervening sequence WQTGT (SEQ ID No: 20) from the β6 fragment also binds to ERK2 (see Example)). To test whether deletion of SQWNND (SEQ ID No: 27) from the β2 fragment had any effect, the peptide KEKLKNPLFK (SEQ ID No: 10) (designated β2 (10(4)) was synthesised and incubated with ERK2. As shown in FIG. 3, the peptide was bound by ERK2.

Figure 4:
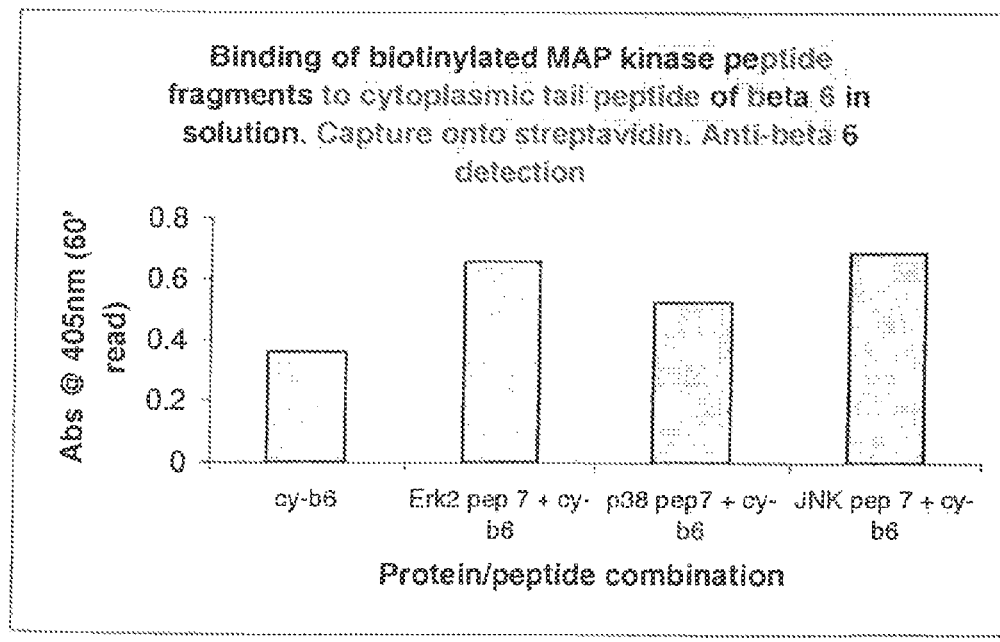
FIG. 4 is a graph showing the binding of the MAP kinases ERK2, p38 and JNK-1 to the cytoplasmic domain of β6.

Next, fragments of ERK2, p38 MAP kinase and JNK-1 MAP kinases were tested for ability to bind with the cytoplasmic domain fragment of β6 HDRKEVAKFEAER-SKAKWQTGTNPLYRGSTSTFKNVTYKHREKQKVDL-STDC (SEQ ID No: 26). The amino acid sequence for the ERK2 fragment used is HRDLKPSNLLLNTTCDLKICD-FGLAR (SEQ ID No: 28) while that for the p38 MAP kinase and JNK-1 MAP kinase fragments are HRDLKPSN-LAVNEDCELKILDFGLAR (SEQ ID No: 29) and HRDLKPSNIVVKSDCTLKILDFGLAR (SEQ ID No: 30), respectively. The results are shown in FIG. 4. All of the MAP kinase fragments bound to the β6 cytoplasmic domain.

EXAMPLE 2

Effect of the Carrier Moiety on Inhibition of HT29 Cancer Cell Activity 2.1: Cell Proliferation Assay Using MTT An assay using the substrate methylthiazoletetrazolium (MTT) was utilised to determine the inhibitory affect of peptide agents on cancer cell proliferation. MTT substrate (CAT No. M-2128, Sigma) is cleaved in growing cells to yield a water insoluble salt. After solubilisation of the salt, a coloured product is produced that allows quantitation of the proliferative activity of the cultured cells. To prepare the MTT solution for use in the assay, 100 mg of MTT is mixed with 20 ml of PBS at pH 7.4. The resulting solution is filter sterilised (0.2 μM syringe filter) and stored at 4° C. protected from light until use.

Cells from the colon cancer cell line HT29 were seeded into wells of a 96-well microlitre plate in Dulbecco's Modified Eagle's Medium (DMEM) supplemented with 10% foetal bovine serum, glutamine, Hepes, and antibiotics at a concentration of 2,000 cells/100 μl and cultured for 24 hours in 5% $CO_2$ in air at 37° C. After the 24 hour incubation period the test agent (solubilised in complete DMEM) is added to test wells to a final media volume of 200 μl and the microtitre plate is incubated for a further 48 to 72 hour period.

A 20 μl volume of the MTT solution prepared as above is then added to the test wells and the microtitre plate incubated for further 3 hours in 5% $CO_2$ in air at 37° C. The plate is subsequently centrifuged for 5 minutes at 2,000 rpm in a microplate carrier. The supernatant is then removed from the wells using a multichannel pipette leaving MTT crystals in the wells.

To the wells is then added 150 μl of 6:1 v/v DMSO/glycine solution (0.1 M glycine and 0.1 M NaCl adjusted to pH 10.5 using NaOH) and the MTT crystals are dissolved by gently vortexing the microtitre plate. Absorbance is read at 550 nm using a microtitre plate reader. The percentage inhibition of proliferation of the test cells is calculated relative to untreated control cells.

2.2: Synthesis and Testing of Peptide Agents

Cells from the colon cancer cell line HT29 express β6. To assess the effect of carrier moieties on inhibition of cellular activity of HT29 cells by peptides which bind to ERK2, peptides comprising the β6 fragment RSKAKWQTGT-NPLYR (SEQ ID No: 4) linked directly to the β3 signal peptide VTVLALGALAGVGVG (SEQ ID No: 2) (Liu et al, PNAS (1996) 93: 11819-11824) or AAVALLPAVLLALLA (SEQ ID No: 1) (designated nfkb) in which the terminal proline of the K-FGF signal peptide AAVALLPAVLLALLA P (designated nfkbp) (U.S. Pat. No. 6,248,558) has been deleted were synthesised as follows:

```
(Frag 5B3)
                                       (SEQ ID No: 31)
VTVLALGALAGVGVGRSKAKWQTGTNPLYR (Frag 5 nfkb)
                                       (SEQ ID No: 19)
AAVALLPAVLLALLARSKAKWQTGTNPLYR
```

Figure 5:
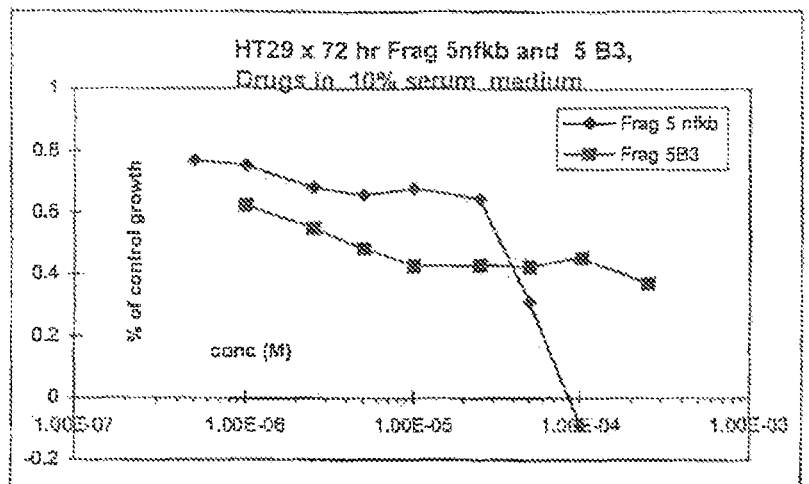
FIG. 5 is a graph showing the inhibition of the activity of HT29 colon cancer cells by a peptide comprising the binding domain of β6 for ERK2 linked to the β3 signal peptide or the modified K-FGF signal peptide AAVALLPAVLLALLA (SEQ ID No: 1)

The inhibition of the activity of the HT29 cells by the synthetic peptides was assessed using the cell proliferation assay described in Example 2.1 and the results are shown in FIG. 5. Use of the modified K-FGF signal peptide resulted in total inhibition of the proliferation of the HT29 colon cancer cells at the higher concentration of the peptides used. In contrast, use of the β3 signal peptide resulted in a decrease in proliferation of the cells to only about 37% of that of the control cells.

Figure 6:
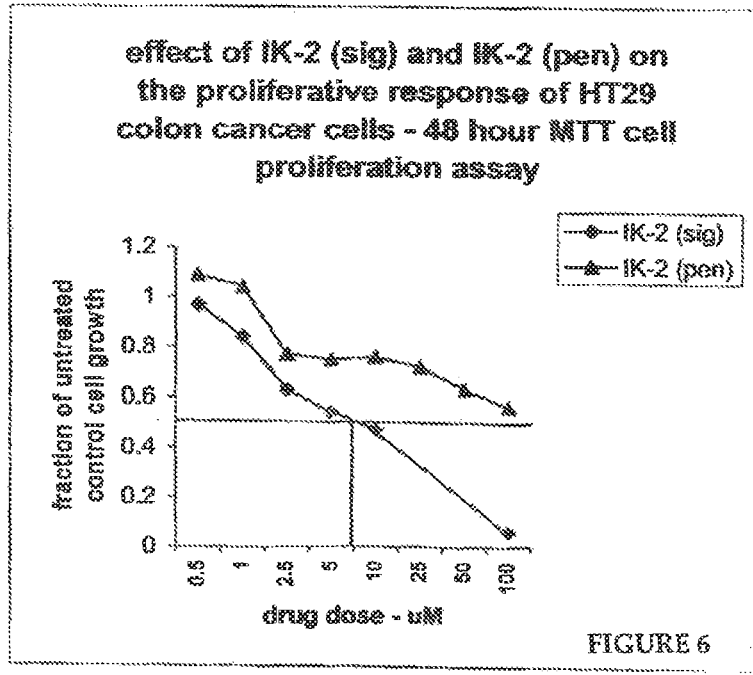
FIG. 6 is a graph showing the inhibition of HT29 colon cancer cells using the peptide RSKAKNPLYR (SEQ ID No: 7) linked to penetratin or the modified K-FGF signal peptide AAVALLPAVLLALLA (SEQ ID No: 1)

Synthetic peptides comprising the 10(4) peptide RSKAKNPLYR (SEQ ID No: 7) linked directly to penetratin or the modified K-FGF signal peptide AAVALLPAVL-LALLA (SEQ ID No: 1) were also prepared and their inhibitory effect of the proliferation of the HT29 colon cancer cells assessed as described above. The complete sequences for these peptides are as below and the results are shown in FIG. 6.

```
(IK-2 (sig))
                                       (SEQ ID No: 16)
AAVALLPAVLLALLARSKAKNPLYR (Ik-2 (pen))
                                       (SEQ ID No: 32)
RQIKIWFQNRRMKWKKRSKAKNPLYR
```

A greater degree of inhibition was observed using the modified K-FGF signal peptide at all concentrations of the synthetic peptides tested.

Figure 7:
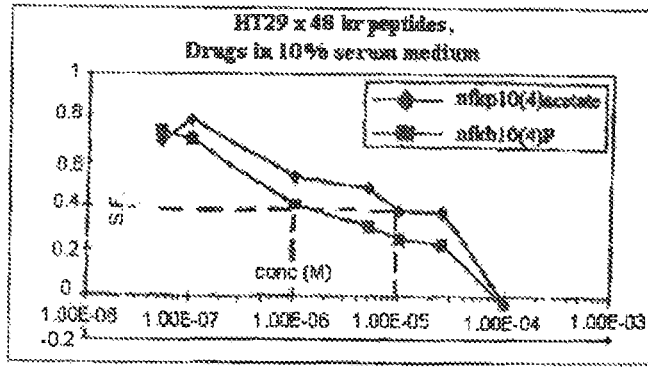
FIG. 7 is a graph showing a comparison of the inhibitory effect of the peptide RSKAKNPLYR (SEQ ID No: 7) linked to K-FGF signal peptide with and without a terminal proline residue on the proliferation of HT29 colon cancer cells.

A comparison of the inhibitory effect of the 10(4) peptide RSKAKNPLYR linked to the K-FGF signal peptide with and without the terminal proline residue on the proliferation of the HT29 cells is shown in the FIG. 7. The complete sequences for the peptides are as follows:

```
(nfkb10(4)acetate)
                                       (SEQ ID No: 16)
AAVALLPAVLLALLARSKAKNPLYR (nfkb10(4)p)
                                       (SEQ ID No: 18)
AAVALLPAVLLALLAPRSKAKNPLYR
```

As indicated in FIG. 7, the presence of the terminal proline of the K-FGF signal peptide resulted in a greater degree of inhibition of proliferation of the HT29 cells over the concentrations of the peptides used with total inhibition being achieved by both synthetic peptides at the highest concentration employed.

Figure 8:
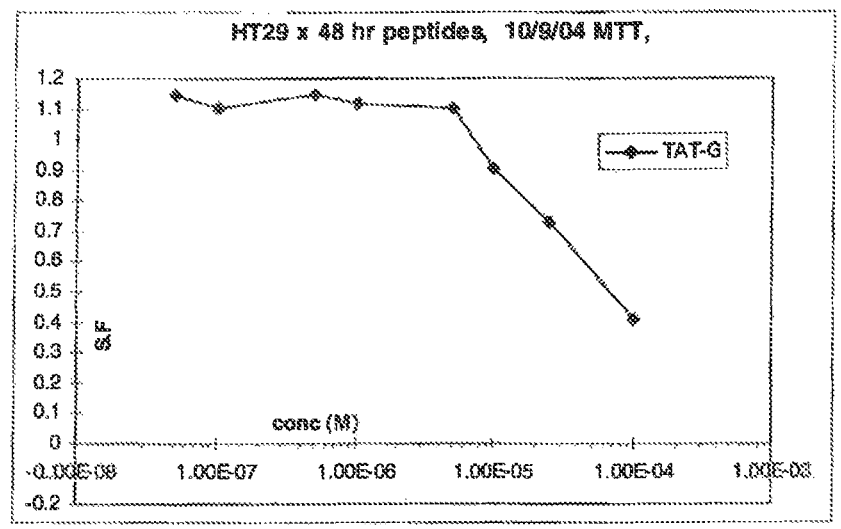
FIG. 8 is a graph showing toxicity of the HIV-TAT carrier peptide GRKKRRQRRRPPQG (SEQ ID No: 14) in HT29 colon cancer cells.
Figure 9:
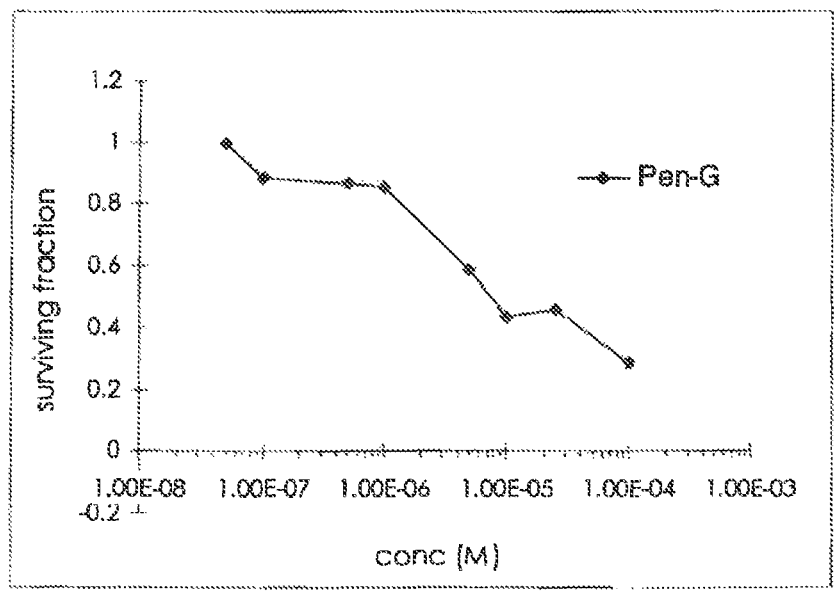
FIG. 9 is a graph showing toxicity of penetratin (RQIKIWFQNRRMKWKKG) (SEQ ID No: 15) in HT29 colon cancer cells.

A study was also undertaken to evaluate the toxicity of HIV-TAT (TAT-G) carrier peptide and penetratin (PEN-G) alone on HT29 colon cancer cells. The results are shown in FIG. 8 and FIG. 9. The complete amino acid sequences for TAT-G and PEN-G are as follows:

(TAT-G)
GRKKRRQRRRPQCG (SEQ ID No: 33)

(PEN-G)
RQIKIWFQNRRMKWKKG (SEQ ID No: 15)

As shown in those figures, both the HIV-TAT carrier peptide and penetratin exhibit some toxicity on HT29 colon cancer cells. The signal peptides AAVALLPAVLLALLA (SEQ ID No: 1) and AAVALLPAVLLALLAP (SEQ ID No: 3) alone have essentially no effect on the proliferation of any cancer cell lines tested (data not shown).

Figure 10:
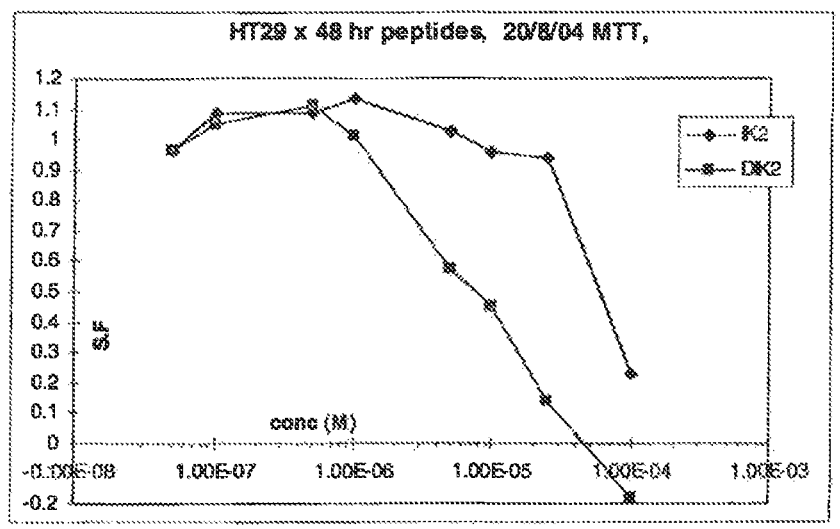
FIG. 10 is a graph showing a comparison of the inhibitory effect of the peptide AAVALLPAVLLALLARSKAKNPLYR (SEQ ID No: 16) on HT29 colon cancer cells and the same peptide in which the entire sequence of the peptide is comprised of D amino acids.

FIG. 10 shows a comparison of the inhibitory effect of peptide AAVALLPAVLLALLARSKAKNPLYR (IK-2) (SEQ ID No: 16) on HT29 colon cancer cells and the same peptide in which the entire sequence is comprised of D amino acids (DIK-2). The DIK-2 peptide was found to be considerably more effective at concentrations of 1 µM and greater.

Figure 11:
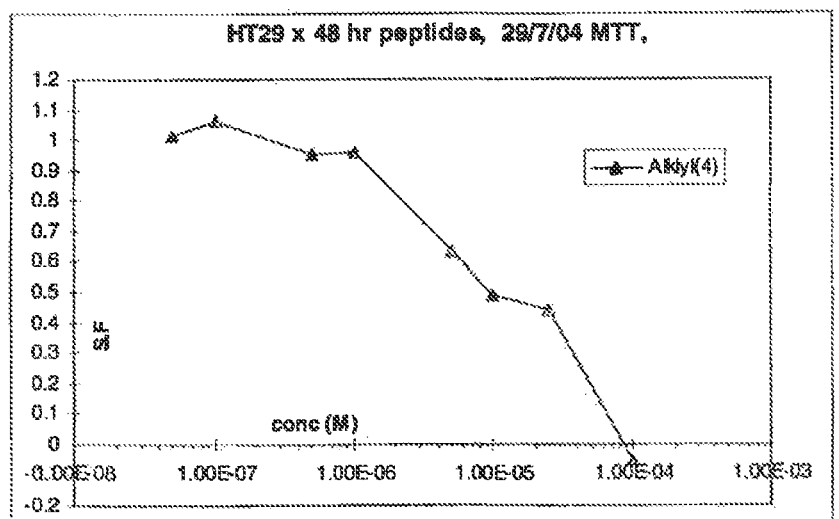
FIG. 11 is a graph showing the inhibitory effect of the peptide RSKAKNPLYR (SEQ ID No: 7) coupled to stearic acid on HT29 colon cancer cells.

FIG. 11 shows that stearic acid coupled to the RSKAKNPLYR (Alkyl(4)) (SEQ ID No: 7) peptide is also effective in facilitating transport of the RSKAKNPLYR (SEQ ID No: 7) peptide into HT29 colon cancer cells and so may be a possible alternative to the use of signal peptides for passage across the outer membrane of cells. The data shown is relative to untreated control cells.

EXAMPLE 3

Inhibition of β6 Expressing and Non-Expressing Cells 3.1 FACScan Analysis

Different cell lines were assessed for β3, β5 and β6 expression by FACScan analysis. Briefly, monolayer cultures of the cells were harvested with trypsin/EDTA. Cells were washed once with PBS, incubated with primary antibody against integrin subunits for 20 minutes at 4° C. and then washed twice with PBS. Cells were then stained with secondary antibody conjugated with phycoerythrin for 20 minutes at 4° C., washed twice with PBS and resuspended in 0.5 ml PBS prior to FACScan analysis (Becton Dickenson, Rutherford, N.J., USA).

Figure 12O:
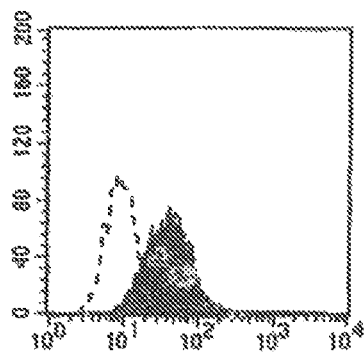
FIGS. 12O, 12P, and 12Q show FACScan analysis results for HMEC-1 endothelial cells.
Figure 12P:
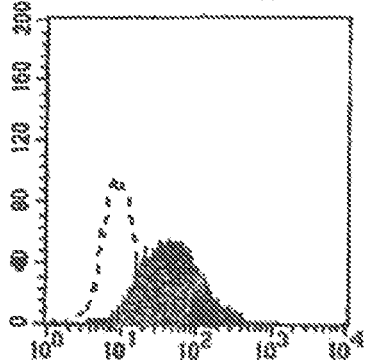
Figure 12Q:
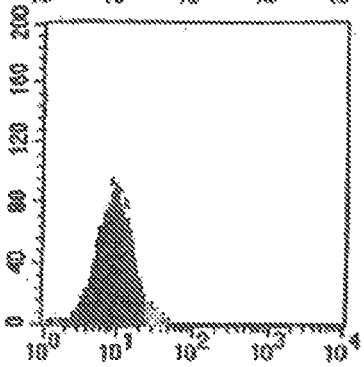
Figure 13A:
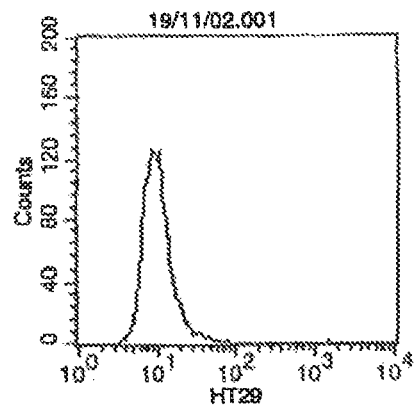
FIGS. 13A, 13B, and 13C show FACScan analysis results for HT29 colon cancer cells.
Figure 13B:
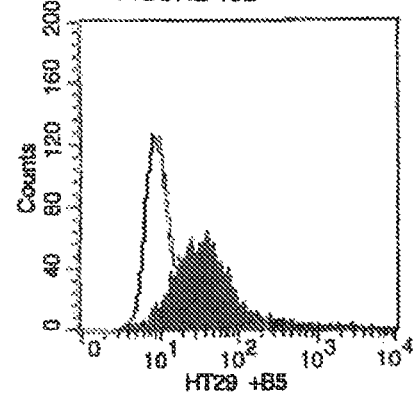
Figure 13C:
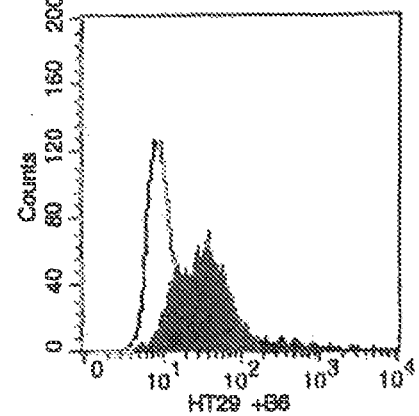
Figure 13D:
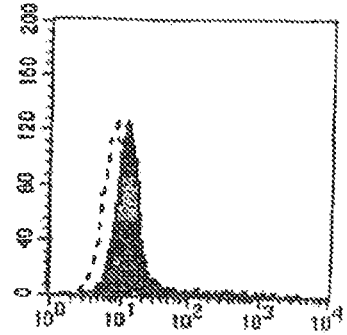
FIGS. 13D and 13E show FACScan analysis results for H460 lung cancer cells.
Figure 13E:
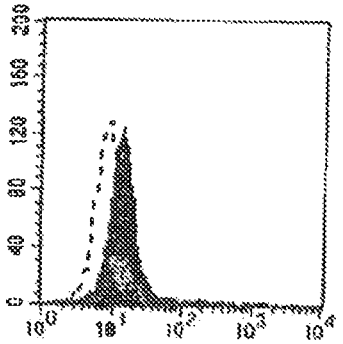
Figure 13F:
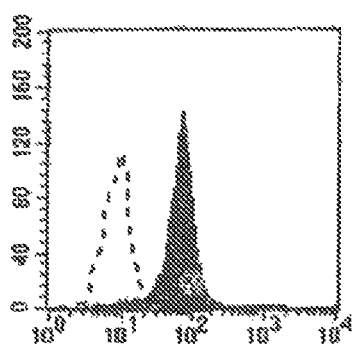
FIGS. 13F, 13G, and 13H show FACScan analysis results for melanoma cells.
Figure 13G:
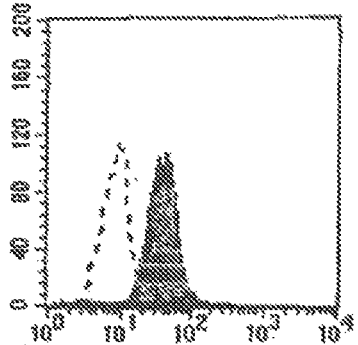
Figure 13H:
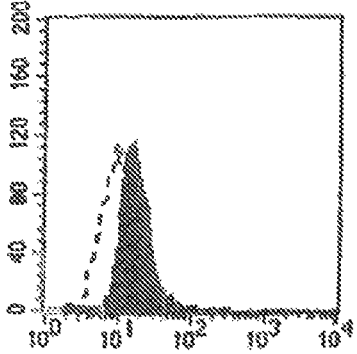

FACScan results for normal human umbilical vein endothelial cells (HUVEC), the neuroblastoma cell line SH-SY5Y, the leukemia cell line HL60, the prostate cancer cell line was DU 145 and the HMEC-1 cell line are shown in FIG. 12A to 12Q, respectively. HMEC-1 cells are malignant HUVEC cells which have been transformed with the virus SV40. As indicated in the graphs shown, all of these cell lines are essentially non-β6 expressing cells but do express β3 and β5 with the exception of the SH-SY5Y cell line which is also essentially non-β5 expressing. In contrast, the colon cancer cell line HT29, the lung cancer cell line H460, and the melanoma cell line WM 115 are all β6 expressing cells as shown in FIG. 13A to 13H, respectively. The breast cancer cell line MCF-7 is also β6 expressing (data not shown).

3.2 Inhibition of Cell Proliferation

The ability of the 10(4) peptide RSKAKNPLYR (SEQ ID No: 7) linked to the signal peptide AAVALLPAVLLALLA (SEQ ID No: 1) to inhibit the proliferation of the above cell lines was assessed using the cell proliferation assay described in Example 2.1.

Figure 14A:
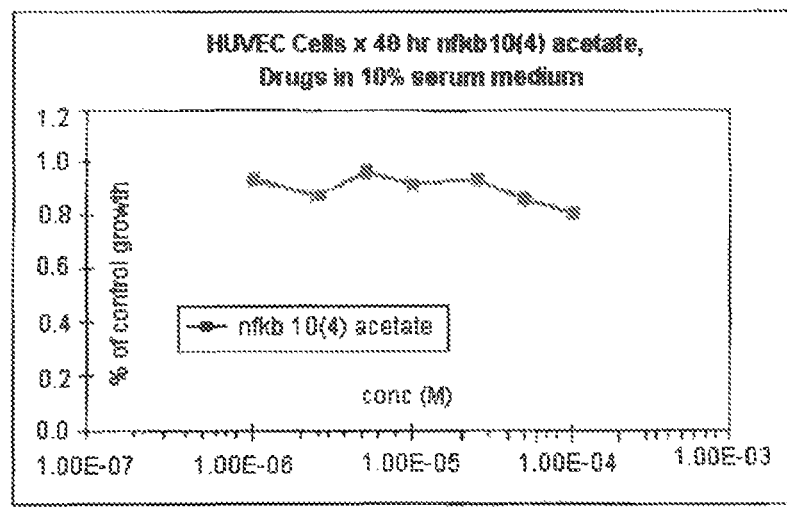
FIGS. 14A, 14B, 14C, 14D, 14E, and 14F are graphs showing the activity of the peptide RSKAKNPLYR (SEQ ID No: 7) linked to the modified K-FGF signal peptide AAVALLPAVLLALLA (SEQ ID No: 1) on different cell lines (A) HUVEC cells, (B) leukemia cells, (C) prostate cancer cells, (D) malignant HUVEC cells, (E) lung cancer cells, and (F) melanoma cells.
Figure 14B:
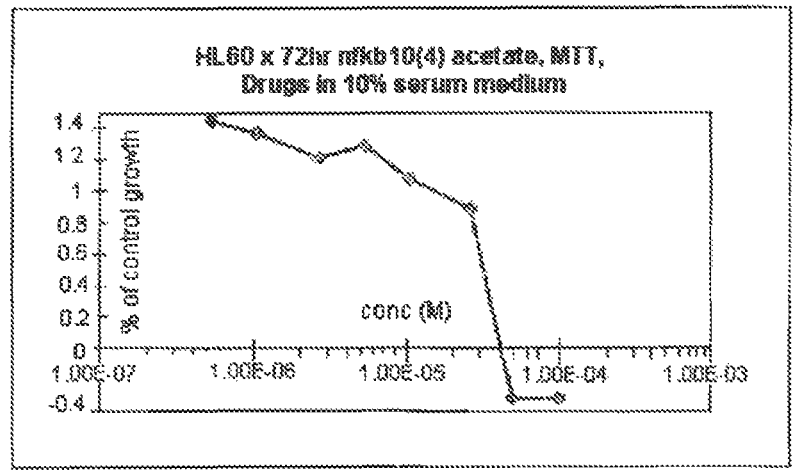
Figure 14C:
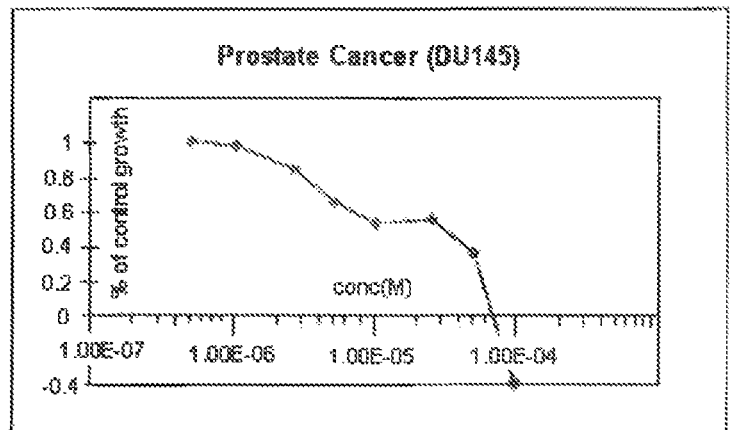
Figure 14D:
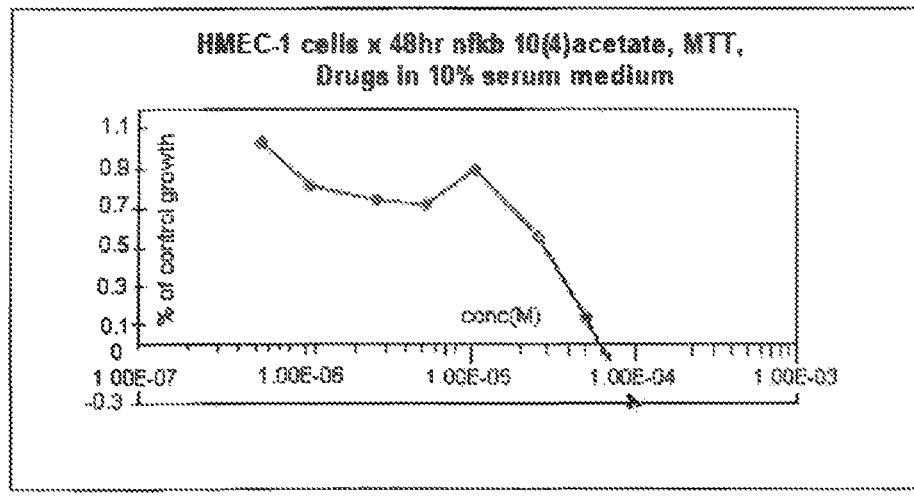
Figure 14E:
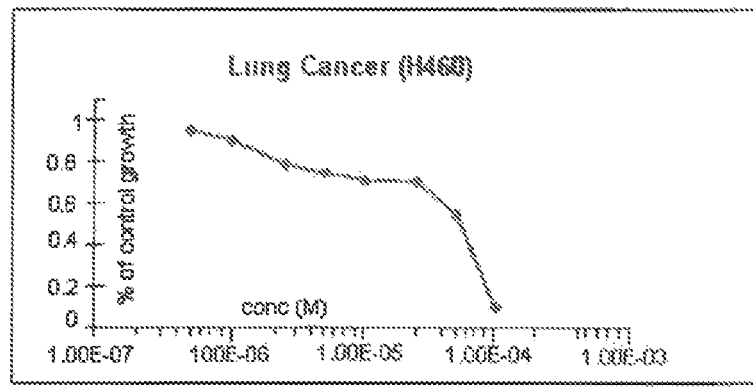
Figure 14F:
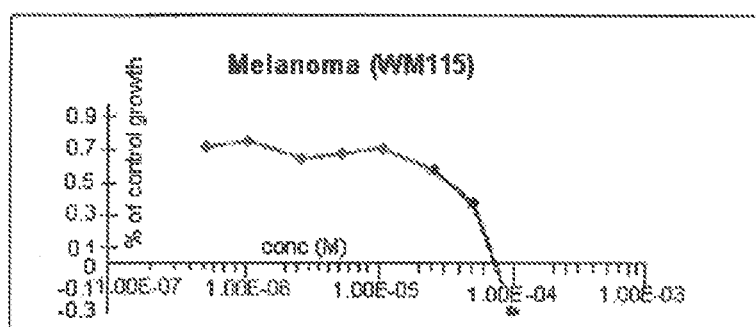
Figure 14G:
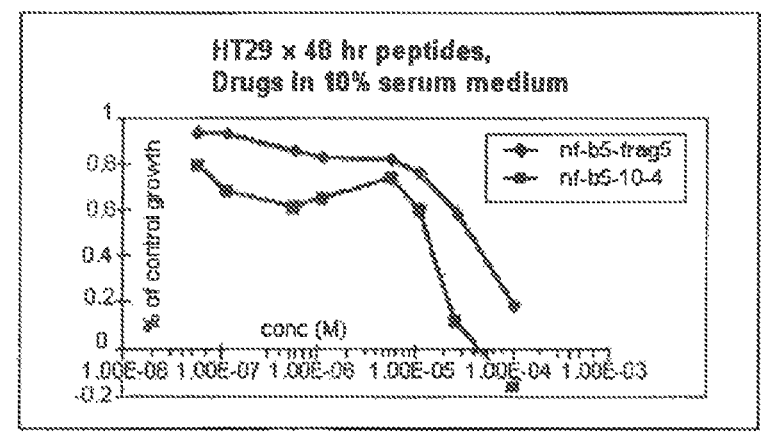
FIG. 14G is a graph showing the activity of the AAVALL-PAVLLALLARSRARNPLYR (SEQ ID No: 17) peptide on HT29 colon cancer cells compared to the β5 peptide RSRARYEMASNPLYR (SEQ ID No: 6) linked to the same signal peptide.

As shown in FIG. 14A, administration of the peptide agent to HUVEC cells has essentially no impact on the proliferation of cells. In contrast, administration of the peptide agent to the leukaemia cell line HL60, the prostate cancer cell line DU145 and the HMEC-1 cell line resulted in increasing levels of inhibition of cellular activity as concentrations of the peptide increased with total inhibition of proliferation being observed at the highest concentration of the peptide as indicated in FIG. 14B to FIG. 14D. The same result was found for the lung cancer cell line H460 and the melanoma cell line WM115 using the peptide agent as shown in FIG. 14E and FIG. 14F, respectively. The inhibition of proliferation of HT29 colon cancer cells when treated with the β5 integrin-derived RSRARYEMASNPLYR (SEQ ID No: 6) peptide or RSRARNPLYR (SEQ ID No: 9) linked with the modified signal peptide AAVALLPAVLLALLA (designated nf-b5-frag 5 and nf-b5-10-4, respectively) is shown in FIG. 14G. While both peptides inhibited proliferation of the cells, a greater degree of inhibition was observed for the peptide agent incorporating RSRARNPLYR.

Figure 14H:
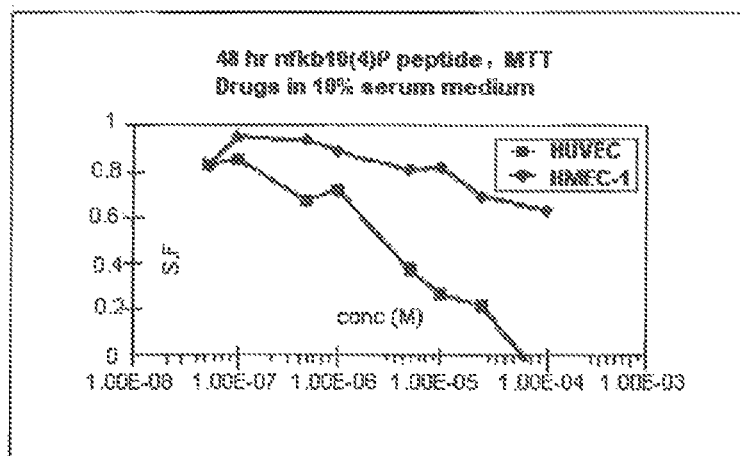
FIG. 14H is a graph comparing the inhibitory effect of the peptide AAVALLPAVLLALLAPRSKAKNPLYR (SEQ ID No: 18) on the proliferation of HUVEC and HMEC-1 cells.

A comparison of the inhibitory effect of the peptide AAVALLPAVLLALLAPRSKAKNPLYR (SEQ ID No: 18) (nfkb10(4)p) on the proliferation of HUVEC and HMEC-1 cells shown in FIG. 14H. As can be seen, increasing inhibition of proliferation of the HMEC-1 cell line was observed with increasing concentration of the peptide while inhibition of proliferation of the HUVEC cells was relatively minimal.

Figure 14I:
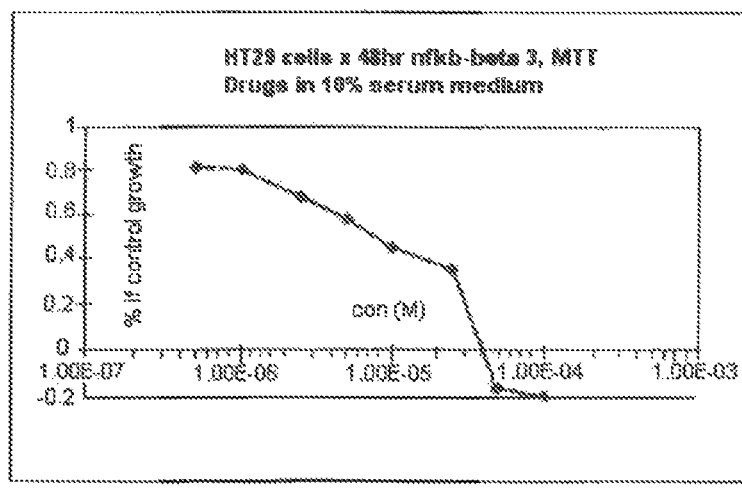
FIG. 14I is a graph showing the inhibitory activity of the β3 peptide RARAKNPLYK (SEQ ID No: 8) linked to AAVALLPAVLLALLA (SEQ ID No: 1) on the proliferation of HT29 colon cancer cells.

Inhibition of proliferation of HT29 cells using a peptide having the amino acid sequence RARAKWDTANNPLYK (SEQ ID No: 5) comprising the binding domain of β3 (designated nfkb-β3) for ERK2 is shown in FIG. 14I.

Figure 14J:
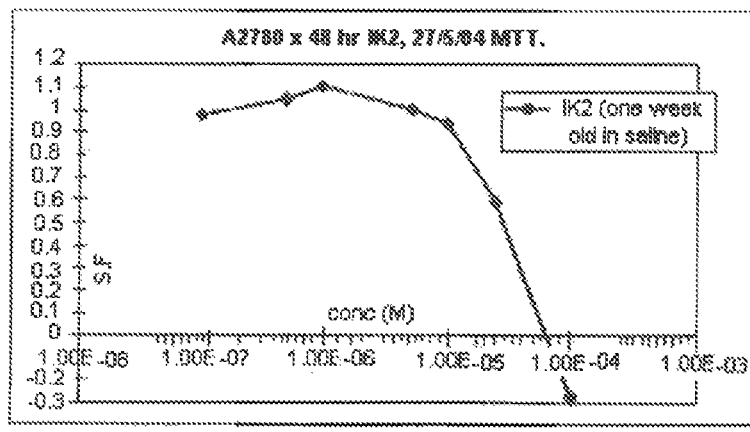
FIGS. 14J and 14K are graphs showing the activity of the peptide AAVALLPAVLLALLARSKAKNPLYR (SEQ ID No: 16) on A2780 ovarian cancer cells, and the cancer cell lines Jurkat, HaCat and HaRas.
Figure 14K:
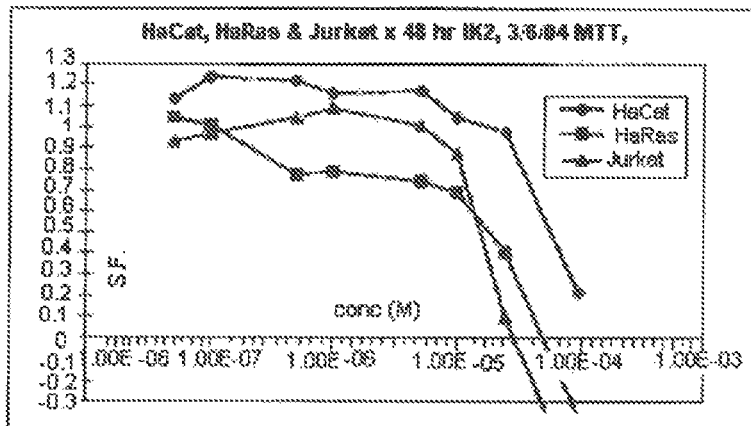

Results for the inhibition of the ovarian cell line A2780 by the peptide AAVALLPAVLLALLARSKAKNPLYR (IK2) (SEQ ID No: 16) relative to control cells are shown in FIG. 14J. Results for the cell lines HaCat, HaRas and the leukeamic T-cell line Jurkat treated with the IK2, are shown in FIG. 14K. HaCat and HaRas cells express β6 (data not shown).

The translocation of phosphatidylserine from the inner layer of the plasma membrane to the outer face of cells is an early indicator of apoptosis. Annexin-V specifically binds to phosphatidylserine. Facscan analysis of HaRas, HaCat and HT29 colon cancer cells, treated with the IK2 peptide and Annexin-V-FITC showed the induction of high levels of apoptosis in these cell lines by the peptide (data not shown).

EXAMPLE 4

Comparison with Conventional Anti-cancer Drugs 4.1: Effect of β6 Cytoplasmic Derived Peptide on HT29 Colon Cancer Cell Proliferation Compared to 5-Fluorouracil (5-FU)

Figure 15:
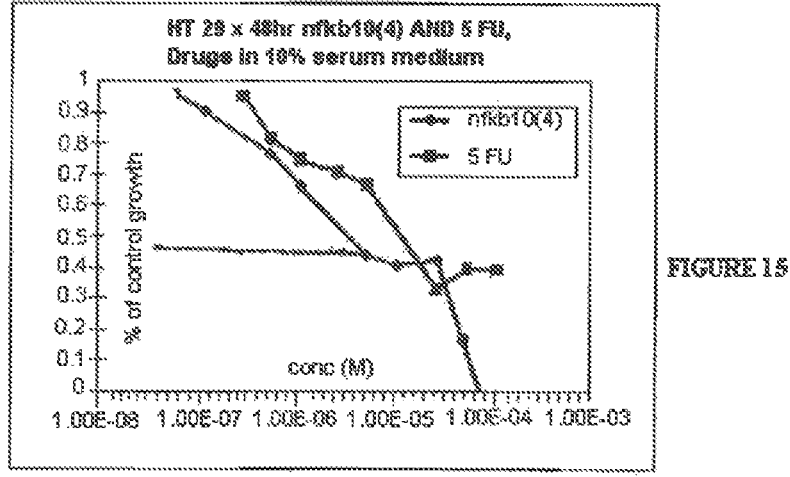
FIG. 15 is a graph showing a comparison of the effect of the peptide AAVALLPAVLLALLAPRSKAKNPLYR (SEQ ID No: 16) compared to 5-fluorouracil on the proliferative response of HT29 colon cancer cells.

HT29 colon cancer cells were treated with either the anti-cancer drug 5-FU or the 10(4) peptide RSKAKNPLYR (SEQ ID No: 7) linked to the K-FGF signal peptide AAVALLPAVLLALLAP (SEQ ID No: 3). As can be seen in FIG. 15, the peptide (designated nfkb10(4)p) was more effective at inhibiting the proliferative response of the HT29 colon cancer cells compared to 5-FU.

Figure 16:
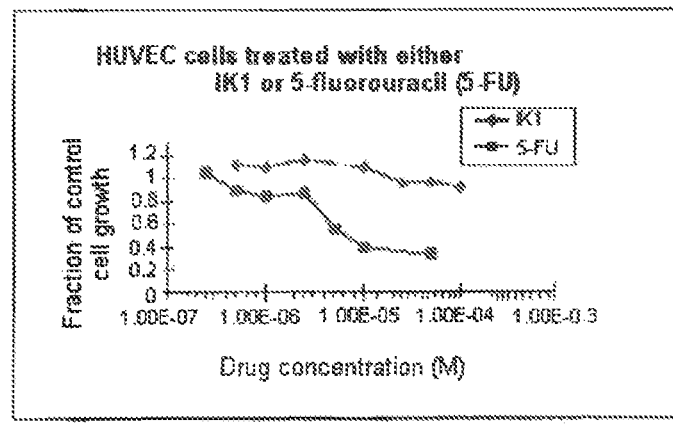
FIG. 16 is a graph comparing the toxicity of the peptides AAVALLPAVLLALLARSKAKWQTGTNPLYR (SEQ ID No: 19) compared to 5-fluorouracil on HUVEC cells.
Figure 17:
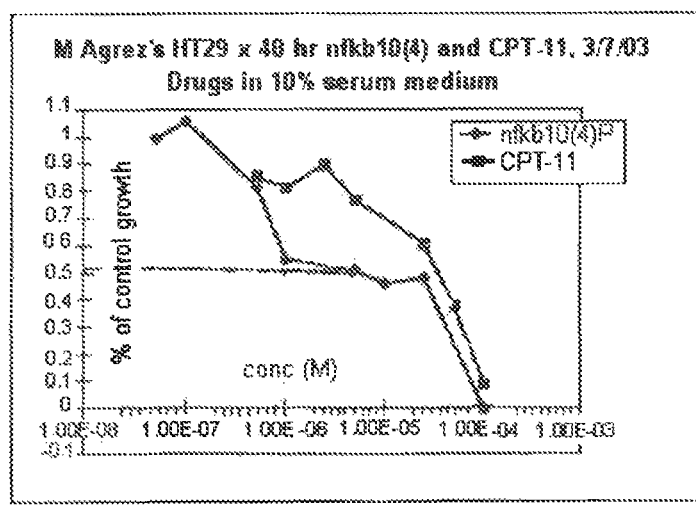
FIG. 17 is a graph comparing the effect of the peptide AAVALLPAVLLALLAPRSKAKNPLYR (SEQ ID No: 18) and the chemotherapeutic agent CPT-11 on the proliferation of HT29 colon cancer cells.

The effect of the AAVALLPAVLLALLARSKAKWQTGTNPLYR (SEQ ID No: 19) peptide agent on normal HUVEC cells compared to 5-FU is shown in FIG. 16. The peptide agent is designated IK-1 in the figure. The graph shows that the peptide has essentially no impact on the cells in contrast to the toxicity of the chemotherapeutic agent 5-FU. FIG. 17 further shows that the 10(4) peptide RSKAKNPLYR (SEQ ID No: 7) linked directly to the K-FGF signal peptide AAVALLPAVLLALLAP (designated nfkb10(4)p in the figure) (SEQ ID No: 3) is more effective in inhibiting proliferation of the colon cancer cell line HT29 compared to the chemotherapeutic agent CPT-11 at all concentrations used.

EXAMPLE 5

Effect of Peptide Agents on In Vivo Tumour Growth

The ability of the peptide agent AAVALLPAVLLALLAR-SKAKWQTGTNPLYR (IK-1) (SEQ ID No: 19) to inhibit tumour growth in immune-deficient Balb/c Nu/Nu mice was assessed.

Balb/c female athymic mice (8 weeks of age obtained from the Animal Resource Centre, Perth, Western Australia) were maintained under pathogen-free conditions and fed standard mouse chow and water ad lib. The mice were divided into groups of ten each. Mice in different groups were marked by ear notching. Briefly, the mice were anaesthetised using isoflurothane by inhalation and their ears marked using a surgical punch. After a recovery period of 48 hours, the mice in each group were injected with $1 \times 10^6$ HT29 colon cancer cells in standard DMEM culture medium subcutaneously dorsally behind the right shoulder using a 21-gauge needle. Animal weights and tumour sizes (breadth and length measured with callipers) were recorded weekly. Mice were sacrificed by $CO_2$ asphyxiation and tumour mass excised for measurement.

Mice were injected twice weekly for four weeks commencing 10 days after tumour cell inoculation with DMEM, signal peptide (AAVALLPAVLLALLA) (designated "carrier") (SEQ ID No: 1) or the AAVALLPAVLLALLAR-SKAKWQTGTNPLYR (IK-1) (SEQ ID No: 19) peptide agent, and tumour growth was compared to an untreated control group.

Figure 18A:
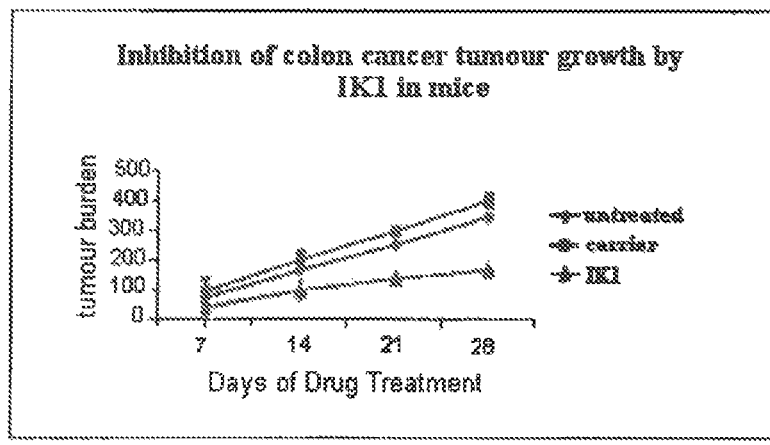
FIGS. 18A and 18B are graphs showing the effect of the intra-tumoural injection of mice with the peptide AAVALL-PAVLLALLARSKAKWQTGTNPLYR (SEQ ID No: 19) on the tumour growth of HT29 colon cancer cells and mouse weight, respectively.
Figure 18B:
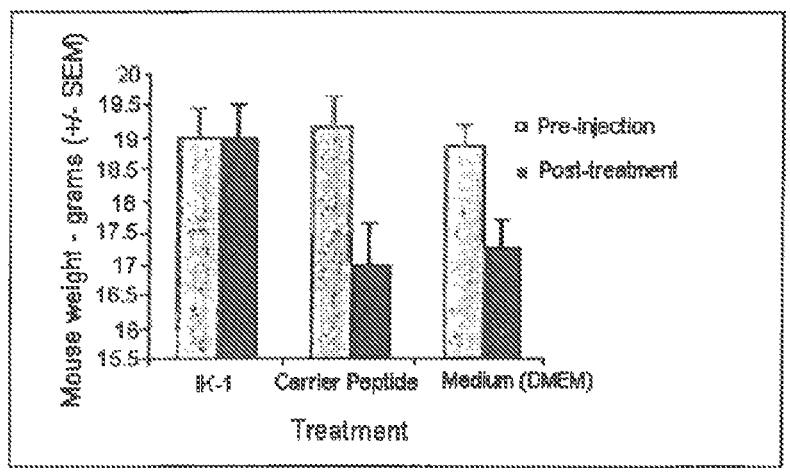
Figure 19:
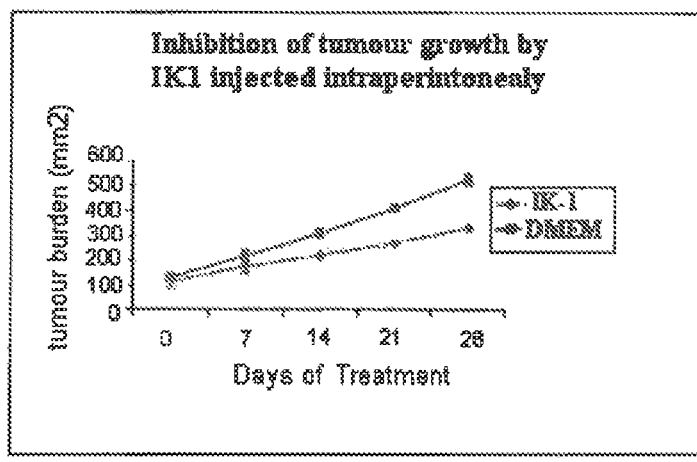
FIG. 19 is a graph showing the effect of the intraperitoneal injection of mice with the peptide AAVALLPAVLLALLAR-SKAKWQTGTNPLYR (SEQ ID No: 19) on the tumour growth of HT29 colon cancer cells.

FIG. 18A and FIG. 18B show tumour growth and mouse weight for mice which received intra-tumoural injections, respectively. Tumour growth in mice which received carrier peptide or DMEM was greater than the untreated control mice group indicating the carrier peptide and culture medium provided a nutrient source for the tumours. In contrast, mice treated with the IK-1 peptide agent showed marked inhibition of tumour growth compared to the untreated control group. Substantially no difference in mouse weight was observed for the untreated and IK-1 treated mice groups at day 28 relative to time 0 (FIG. 18B). However, mice in the carrier peptide and DMEM treated groups showed marked weight loss compared to the control group at day 28. Inhibition of tumour growth was observed for mice injected intra-peritoneally with the peptide agent as shown in FIG. 19.

Figure 20:
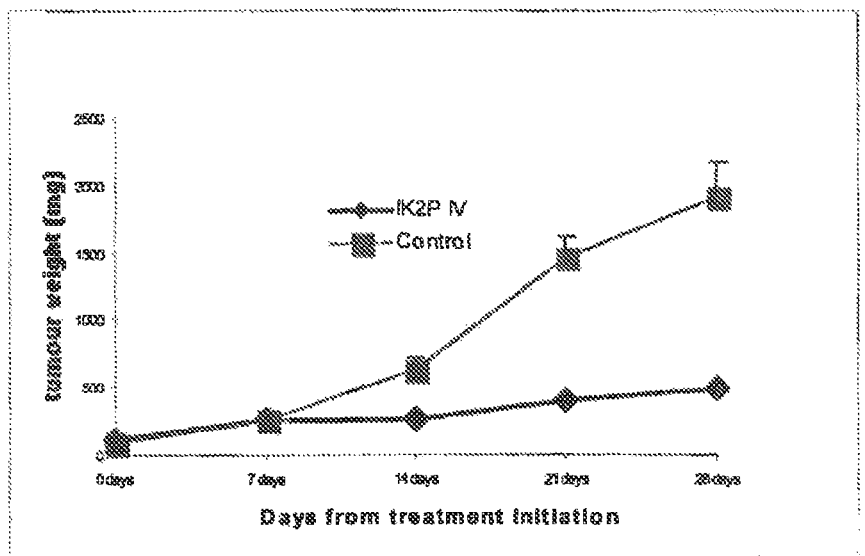
FIG. 20 is a graph showing inhibition of bowel cancer xenografts by the peptide AAVALLPAVLLALLAPR-SKAKNPLYR (SEQ ID No: 18) administered intravenously to tumour bearing mice.

Colon cancer inhibition by peptide AAVALLPAVLLAL-LAPRSKAKNPLYR (IK2P) (SEQ ID No: 18) administered intravenously to colon tumour bearing Balb/c athymic mice as per the protocol described above, is shown in FIG. 20. Colon tumour xenografts were achieved by injection of $1 \times 10^6$ HT29 colon cancer cells as above. Tumour growth in mice treated with the IK2P peptide was significantly reduced compared to control mice treated with DMEM alone.

Figure 21:
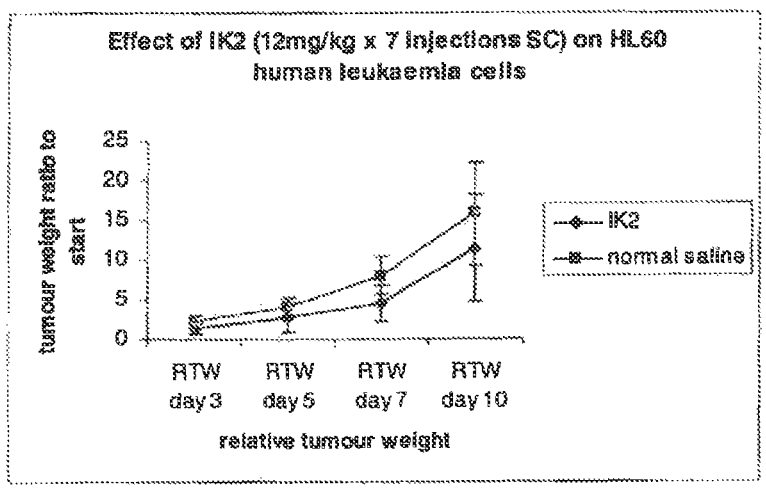
FIG. 21 is a graph showing inhibition of HL60 leukaemia xenografts by the peptide AAVALLPAVLLALLAPR-SKAKNPLYR (SEQ ID No: 18) administered subcutaneously to tumour bearing mice.

The inhibition of HL60 leukaemia xenografts in Balb/c female athymic mice by the peptide AAVALLPAVLLAL-LARSKAKNPLYR (SEQ ID No: 16) administered subcutaneously is shown in FIG. 21. Mice were given a single injection of the IK2 peptide (12 mg/Kg) subcutaneously on each of 7 consecutive days. Tumour weight relative to control mice treated with saline alone are shown. Tumours weights in mice treated with the IK2 peptide were markedly reduced compared to tumours in control mice.

Figure 22:
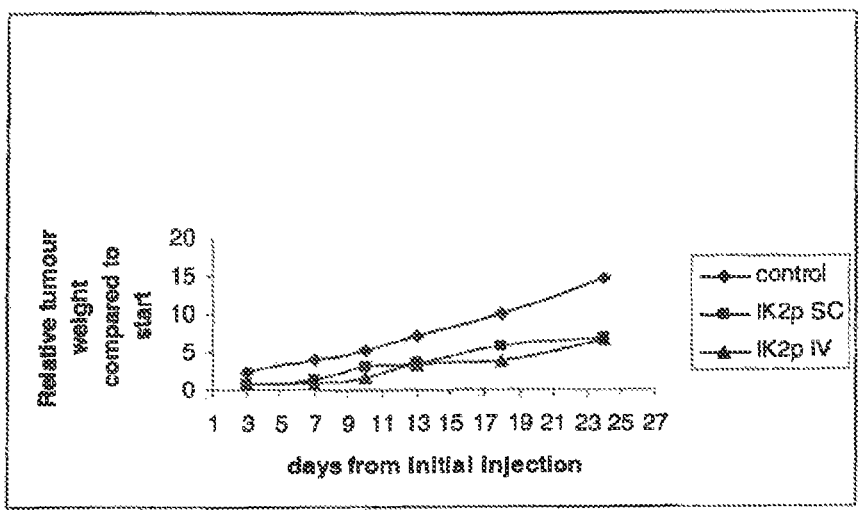
FIG. 22 is a graph showing the efficacy of the peptide AAVALLPAVLLALLAPRSKAKNPLYR (SEQ ID No: 18) administered intravenously or subcutaneously to mice bearing HT29 colon cancer xenografts.

A comparison of the efficacy of IK2P peptide (SEQ ID No: 18) administered as a single injection on each of 5 consecutive days either intravenously (IV) or subcutaneously (SC) against HT29 colon cancer xenographs in Balb/c athymic mice is shown in FIG. 22. As can be seen, similar results were obtained for the intravenous and subcutaneous routes of administration compared to control mice.

EXAMPLE 6

Selective Killing of HT29 Colon Cancer Cells by IK2 Peptide

The killing of HT29 cancer cells compared to normal keratinocytes, human umbilical vein epithelial cells (HU-VECs) and skin fibroblasts by the peptide AAVALLPAVL-LALLARSKAKNPLYR (IK2) (SEQ ID No: 16) was assessed. Briefly, cells were recovered by trypsinisation and resuspended into fresh culture medium. Cell viability was determined (0.4% Trypan Blue in phosphate buffered saline (PBS) 1:1 v/v), and $0.75 \times 10^6$ viable cells were passaged into a 25 cm$^2$ tissue culture flask then cultured for 24 hours at 37° C., 5% $CO_2$ in air. Immediately prior to the addition of the IK2 peptide, culture media was removed by decanting and replaced with fresh media (2.0 mls minus volume addition of IK2 peptide). The treated cells were then cultured for 16 hours.

Cells were prepared as above for the positive control. Staurosporine (Sigma #S5921) was added to the culture media to a final concentration of 1 μM and the cells exposed to the apoptosis inducer for a maximum of 1-2 hours. For a negative control, vehicle alone (normal saline) was added to cell culture media.

Apoptotic cells were detected by FACScan analysis utilising Annexin-V-FITC (Sigma kit #A2214) to indicate apoptosis. For the analysis, cells were recovered by trypsinisation as above, and resuspended (~$1 \times 10^6$ cells/ml) into 1× binding buffer (Sigma #B9796). 500 μl of cell suspension was then aliquoted into a 10 ml plastic test tube, prior to the addition of 5 μl of Annexin-V FITC and 10 μl of propidium iodide (Sigma #P2667). Cells were incubated at room temperature for 10 minutes in the dark and fluorescence determined by flow cytometer. Living cells are not stained by either Annexin-V-FITC or propidium iodide, while early apoptosis is indicated by staining with Annexin-V-FITC only and necrotic cells are stained by both Annexin-V-FITC and propidium iodide.

FIG. 23 shows that apoptosis was induced in the HT29 colon cancer cell line by both staurosporin and the IK2 peptide. In contrast, while staurosporim also induced apoptosis in the keratinocytes (KC), HUVEC and skin fibroblast (SkinF) cells, essentially no apoptosis was induced in these cells by the IK2 peptide indicating specificity of the peptide for killing the HT29 colon cancer cells compared to normal cells. The finding that malignant HMEC-1 cells but not normal HUVEC cells are inhibited by the IK2 peptide also shows selectivity of the peptide agent against those cancer cells.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Agrez, M. V., Bates R. C., Mitchell, D., Wilson, N., Ferguson, N., Anseline, P. and Sheppard. D., Multiplicity of fibronectin-binding αv integrin receptors in colorectal cancer. Br. J. Cancer 73, 887-892 (1996).
2. Agrez, M. V., Gu, X., Turton, J., Meldrum, C., Niu, J., Antalis, T. and Howard, E. W., The αvβ6 integrin induces gelatinase B secretion in colon cancer cells. Int. J. Cancer 81, 90-97 (1999).
3. Bachmann, A. S., Surovoy, A., Jung, G. and Moelling, K., Integrin receptor-targeted transfer peptides for efficient delivery of antisense oligodeoxynucleotides. J. Mol. Med. 76, 126-132 (1998).
4. Boulton, T. G., Nye, S. H. and Robbins, D. J., ERKs: a family of protein-serinethreonine kinases that are activated and tyrosine phosphorylated in response to insulin and NGF. Cell 65, 663-675 (1991).
5. Breuss, J. M., Gallo, J., De Lisser, H. M., Klimanskaya, I. V., Folkesson, H. G., Pittet, J. F., Nishimura, S. L., Aldape, K., Landers, D. V., Carrenter, W., Gillet, N., Sheppard, D., Mathay, M., Albeda, S. M., Kramer, R. H., and Pytela, R., Expression of the β6 integrin in development, neoplasia and tissue repair suggests a role in epithelial remodelling. J. Cell Sci. 108, 2241-2251 (1995).
6. Breuss, J. M., Gillet, N., Lu, L., Sheppard, D. and Pytela, R., Restricted distribution of integrin beta 6 mRNA in primate epithelial tissues. J. Histochem. Cytochem. 41, 1521-1527 (1993).
7. Cone, R. I., Weinacker, A., Chen, A. and Sheppard, D., Effects of beta subunit cytoplasmic domain deletions on the recruitment of the integrin alpha v beta 6 to focal contacts. Cell Adhes. Comm. 2, 101-113 (1994).
8. Derossi, D., Calvet, S., Trembleau, A., et al, Cell internalization of the third helix of the Antennapedia homeo domain is receptor-independent. J. Biol. Chem. 271, 18188-18193 (1996).
9. Derossi, D., Joliot, A. H., Chassaing, G. and Prochiantz, A., The third helix of the Antennapedia homeodomain translocates through biological membranes. J. Biol. Chem. 269, 10444-10450 (1994).
10. Garrington, T. P., and Johnson, G. L., Organization and regulation of mitogen-activated protein kinase signaling pathways. Curr. Opin. Cell Biol. 11, 211-218 (1999).
11. Giancotti, F. G. and Ruoslahti, E., Integrin signalling. Science 285, 1028-1032 (1999).
12. Haapasalmi, K., Zhang, K., Tonneson, M., Olerud, J., Sheppard, D., Salo, T., Kramer, R., Clark, R. A. F., Uitlo, V-J. and Larjava, H., Keratinocytes in human wounds express avb6 integrin. J. Invest. Dermatol. 106, 42-48 (1996).
13. He, T-C., Zhou, S., Da Costa, L. T., Yu, J., Kinzler, K. W. and Vogelstein, B. A simplified system for generating recombinant adenoviruses. Proc., Natl. Acad. Sci. USA 95, 2509-2514 (1998).
14. Howe, A., Aplin, A. E., Alahari, S. K. and Juliano, R. L., Integrin signaling and cell growth control. Curr. Opin. Cell Biol. 10, 220-231 (1998)
15. Jones, J., Watt, F. M. and Speight, P. M., Changes in the expression of alpha v integrins in oral squamous cell carcinomas. J. Oral Path. & Med. 26, 63-68 (1997).
16. Reszka, A. A., Hayashi, Y. and Horwitz, A. F., Identification of amino acid sequences in the integrin beta 1 cytoplasmic domain implicated in cytoskeletal association. J. Cell Biol. 117, 1321-1330 (1992).
17. Schiller et al. Int. J. Pept. Prot. Res. 25, 175 (1985).
18. Sheppard, D., Rozzo, C., Starr, L., Quaranta, V., Erle, D. J. and Pytela, R., Complete amino acid sequence of a novel integrin β subunit (β6) identified in epithelial cells using the polymerase chain reaction. J. Biol. Chem. 265, 11502-11507 (1990).
19. Smythe, W. R., Lebel, E., Bavaria, J. E., Kaiser, L. R. and Albelda, S. M., Integrin expression in non-small cell carcinoma of the lung. Cancer & Metastasis Reviews 14, 229-239 (1995).
20. Takiuchi, H., Kanokogi, M., Fujimoto, N., Hanafusa, T., Kyo, M., Ichikawa, Y., Nagano, S., Fukunishi, T., Yabumoto, H. and Ihara, H., Expression of integrin molecule in urological tumour cell lines by using RT-PCR method. Jap. J. Urology 85, 584-588 (1994).
21. Thomas, G. J., Jones, J. and Speight, P. M., Integrins and oral cancer. Oral Oncology 33, 381-388 (1997).

The invention claimed is:

1. A polypeptide comprising amino acid sequence KEKLKNPLFK (SEQ ID No. 10), wherein the polypeptide is 40 amino acids in length or less.

2. The polypeptide according to claim 1, consisting of amino acid sequence KEKLKNPLFK (SEQ ID No: 10).

3. The polypeptide according to claim 1 wherein the polypeptide binds to ERK2 MAP kinase.

4. An agent comprising the polypeptide according to claim 1, coupled to a facilitator moiety for facilitating passage of the polypeptide across the outer cell membrane of cells.

5. The agent according to claim 4 wherein the facilitator moiety is selected from a group consisting of a carrier peptide and a lipid moiety.

6. The agent according to claim 4 being a fusion protein comprising the polypeptide and the facilitator moiety.

7. A pharmaceutical composition comprising a polypeptide according to claim 1 together with a pharmaceutically acceptable carrier or excipient.

8. A pharmaceutical composition comprising an agent according to claim 4 together with a pharmaceutically acceptable carrier or excipient.

* * * * *